(12) United States Patent
Wang et al.

(10) Patent No.: US 12,364,722 B2
(45) Date of Patent: Jul. 22, 2025

(54) **MULTIFUNCTIONAL *LACTOBACILLUS* CAPABLE OF RELIEVING PFOA TOXIC EFFECTS AND APPLICATION THEREOF**

(71) Applicant: Jiangnan University, Wuxi (CN)

(72) Inventors: Gang Wang, Wuxi (CN); Wei Chen, Wuxi (CN); Jianxin Zhao, Wuxi (CN); Hao Zhang, Wuxi (CN); Xi Liang, Wuxi (CN); Qingmin Kong, Wuxi (CN); Qixiao Zhai, Wuxi (CN); Wenwei Lu, Wuxi (CN); Shumao Cui, Wuxi (CN); Bo Yang, Wuxi (CN); Bingyong Mao, Wuxi (CN)

(73) Assignee: Jiangnan University, Wuxi (CN)

( * ) Notice: Subject to any disclaimer, the term of this patent is extended or adjusted under 35 U.S.C. 154(b) by 641 days.

(21) Appl. No.: 17/562,081

(22) Filed: Dec. 27, 2021

(65) Prior Publication Data
US 2022/0152130 A1 May 19, 2022

Related U.S. Application Data

(63) Continuation of application No. PCT/CN2020/098036, filed on Jun. 24, 2020.

(30) Foreign Application Priority Data

Jun. 28, 2019 (CN) .......................... 201910574811.5
Jun. 28, 2019 (CN) .......................... 201910575089.7
Jun. 28, 2019 (CN) .......................... 201910575996.1

(51) Int. Cl.
*A61K 35/747* (2015.01)
*A23L 33/135* (2016.01)
(Continued)

(52) U.S. Cl.
CPC .......... *A61K 35/747* (2013.01); *A23L 33/135* (2016.08); *C12N 1/20* (2013.01); *C12R 2001/225* (2021.05)

(58) Field of Classification Search
CPC ....... A61K 35/747; A23L 33/135; C12N 1/20; C12R 2001/225
See application file for complete search history.

(56) References Cited

FOREIGN PATENT DOCUMENTS

| CN | 105462887 A | 4/2016 |
|---|---|---|
| CN | 107227275 A | 10/2017 |

(Continued)

OTHER PUBLICATIONS

Xing J.L. et al., "Screening of potential probiotic lactic acid bacteria based on gastrointestinal properties and perfluorooctanoate toxicity", Appl Microbiol Biotechnol, vol. 100, Apr. 19, 2016.

(Continued)

*Primary Examiner* — Louise W Humphrey
*Assistant Examiner* — Rachel Emily Martin
(74) *Attorney, Agent, or Firm* — IPro, PLLC; Na Xu

(57) ABSTRACT

The present disclosure discloses multifunctional lactobacilli capable of relieving a toxic effect of perfluorooctanoic acid (PFOA) and use thereof, and belongs to the technical field of microorganisms. *Lactobacillus fermentum* CCFM1051, *Lactobacillus casei* CCFM1052 and *Lactobacillus buchneri* CCFM1053 of the present disclosure have high adsorption effect on PFOA, can significantly relieve liver oxidative stress damage and serum biochemical indicators caused by PFOA, spleen atrophy caused by PFOA exposure, imbalance of intestinal microorganisms caused by PFOA exposure and metabolic disorder of intestinal flora caused by PFOA exposure, significantly increase the content of acetic acid and propionic acid in the intestinal tract, increase the fecal water content and decrease first black stool defecation time (Continued)

of mice with constipation, improve proliferation and MafA gene expression of INS-1 cells under high glucose, have the potential to relieve PFOA-related diabetes, reduce occurrence of liver diseases, metabolic diseases and potential carcinogenicity, and have broad use prospects.

5 Claims, 17 Drawing Sheets

Specification includes a Sequence Listing.

(51) Int. Cl.
    *C12N 1/20*     (2006.01)
    *C12R 1/225*     (2006.01)

(56) References Cited

FOREIGN PATENT DOCUMENTS

| CN | 108018248 A | 5/2018 |
|---|---|---|
| CN | 110226630 A | 9/2019 |
| CN | 110229769 A | 9/2019 |
| CN | 110684682 A | 1/2020 |

OTHER PUBLICATIONS

Koutnikova H. et al., "Impact of bacterial probiotics on obesity diabetes and non-alcoholic fatty liver disease related variables: a systematic review and meta-analysis of randomised controlled trials", BMJ Open, vol. 9, Mar. 30, 2019.

```
                        SEQUENCE LISTING

<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (14)..(14)
<223> OTHER INFORMATION: n is a, c, g, or t

<400> SEQUENCE: 1
aytgggydta aagng                                                  15

<210> SEQ ID NO 2
<211> LENGTH: 18
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: n is a, c, g, or t

<400> SEQUENCE: 2
tacnvgggta tctaatcc                                               18

<210> SEQ ID NO 3
<211> LENGTH: 20
<212> TYPE: DNA
<213> ORGANISM: Artificial Sequence
<220> FEATURE:
<223> OTHER INFORMATION: Synthetic sequence

<400> SEQUENCE: 3
atcactctgc ccaccatcac                                             20

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence

<400> SEQUENCE: 4
atgacctcct ccttgctgaa                                             20
```

MULTIFUNCTIONAL *LACTOBACILLUS* CAPABLE OF RELIEVING PFOA TOXIC EFFECTS AND APPLICATION THEREOF

TECHNICAL FIELD

The disclosure herein relates to multifunctional lactobacilli capable of relieving a toxic effect of perfluorooctanoic acid (PFOA) and use thereof, specifically relates to multifunctional *Lactobacillus fermentum* CCFM1051, *Lactobacillus casei* CCFM1052 and *Lactobacillus buchneri* CCFM1053 capable of relieving a toxic effect of PFOA, and use of any of the above strains or a composition thereof, and belongs to the technical field of microorganisms.

BACKGROUND

A perfluoro compound has good thermal, chemical and biological stability due to hydrophobic and oleophobic properties, and is widely used in various industries, such as ready-to-wear clothes (waterproof and stain-resistant outdoor clothes, etc.), home textiles (carpets, furniture fabrics, etc.), takeaway food containers, personal care products (dental floss, etc.) and fire-extinguishing foam. Perfluorooctanoic acid (PFOA) is one of a final transformation product of various fluorine compounds and can be enriched along a food chain. The PFOA has been detected in various environmental media globally, such as water, soil, atmosphere, dust, animals and humans and has a half-life period of 2-3 years in humans, and thus has received more and more attention by research scholars. In 2013, the PFOA was included in the Candidate List of Substances of Very High Concern by the regulation on the Registration, Evaluation, Authorization and Restriction of Chemicals (REACH regulation) as a persistent, cumulative and toxic chemical substance, and was officially included in the REACH regulation in 2017 and subject to specific controls within the European Union. However, the PFOA is still used in a large amount in some countries. Besides, the residual PFOA in the environment may also have a lasting effect on an entire ecosystem for a long period of time in the future.

A correlation research between the PFOA content in blood of exposed people and a possible health influence finds that an exposure to the PFOA possibly has a more obvious relationship with a rise of a total cholesterol concentration in the blood, a rise of an alanine aminotransferase (ALT) concentration and a reduction of birth weight. It has also been found that the PFOA exposure is associated with a reduced vaccination response. These indications suggest that the PFOA may affect a liver function, lipid metabolism and an immune function in humans. The effects in humans have been clearly found in mammals. The PFOA has various toxic effects such as hepatotoxicity, immunotoxicity, reproductive toxicity, developmental toxicity, neurotoxicity. The PFOA can cause hepatomegaly while inducing oxidative stress of a mouse liver tissue to abnormally increase free radicals, which may be a main cause to liver damage. PFOA exposure causes various degrees of damage to multiple immune organs of an immune system of aquatic animals and rodents, results in atrophy and aging of the spleen and thymus, significantly interferes an expression of interleukin in the spleen of zebrafish, and leads to apoptosis and decline of lymphocytes. In an exposure experiment of an asthmatic mouse, compared with an asthma model group, the high-dose PFOA exposure increased a peripheral blood inflammatory factor IL-4 and obviously decreased IFN-γ, namely inducing a Th2-type immune response to aggravate pulmonary inflammation.

At present, methods for relieving toxicity of the PFOA are mostly based on natural chemical substances with a high antioxidant activity and a relieving function, such as *lycium barbarum* polysaccharides, morin, trihydroxyisoflavone, lycopene and the like. However, these natural substances are expensive and difficult to obtain. Moreover, the potential hazard to humans from a large intake is unknown due to human tolerance. Therefore, there is clearly a need to find an effective way to effectively relieve PFOA toxicity without having other possible deleterious effects on humans.

SUMMARY

The present disclosure discloses any one of the following lactobacilli:

(a) *Lactobacillus fermentum* CCFM1051 has been deposited in Guangdong Microbial Culture Collection Center on Apr. 29, 2019 and has the preservation number of GDMCC No: 60649;

(b) *Lactobacillus casei* CCFM1052 has been deposited in Guangdong Microbial Culture Collection Center on Apr. 29, 2019 and has the preservation number of GDMCC No: 60650; and (c) *Lactobacillus buchneri* CCFM1053 has been deposited in Guangdong Microbial Culture Collection Center on Apr. 29, 2019 and has the preservation number of GDMCC No: 60651.

The present disclosure discloses a composition containing one or more of the lactobacilli.

In one example, the composition is a food, a microbial preparation (a fermentation agent), a medicine or a healthcare product.

In one example, the food is fermented and prepared by fermentation by *Lactobacillus fermentum* CCFM1051, *Lactobacillus casei* CCFM1052 and *Lactobacillus buchneri* CCFM1053 or a mixture of the various lactobacilli.

In one example, the fermented food includes a solid food, a liquid food or a semi-solid food.

In one example, the fermented food includes a dairy product, a bean product, and a fruit and vegetable product.

In one example, the food is a that functional food.

In one example, the dairy products include milk, sour cream, and cheese; and the fruit and vegetable products include cucumber, carrot, beet, celery, and cabbage products.

In one example, the composition is a fermentation agent; and the fermentation agent is liquid or solid.

In one example, the fermentation agent contains lactobacilli of $\geq 1 \times 10^8$ CFU/mL.

In one example, the fermentation agent contains lactobacilli of $\geq 1 \times 10^8$ CFU/g.

In an example, the medicine and contains a pharmaceutically acceptable carrier.

In one example, the pharmaceutically acceptable carrier includes but is not limited to an excipient and a diluent; the excipient includes but is not limited to lactose, dextrose, sucrose, sorbitol, mannitol, starch, arabic gum, calcium phosphate, alginate, tragacanth gum, gelatin, calcium silicate, microcrystalline cellulose, polyvinylpyrrolidone, cellulose, water, syrup and methylcellulose; and the diluent includes but is not limited to normal saline or syrup.

In one example, the medicine at least has one of the following uses:
(a) relieving a toxic effect of perfluorooctanoic acid (PFOA);
(b) preventing, treating or relieving constipation;
(c) preventing liver disease or reducing occurrence of liver disease;
(d) preventing hypertension or lower blood pressure;
(e) preventing obesity or relieving metabolic diseases caused by obesity; and
(f) improving proliferation and MafA gene expression of INS-1 cells under high glucose or alleviating PFOA-related diabetes.

The present disclosure discloses use a composition containing the *Lactobacillus fermentum* CCFM1051, *Lactobacillus casei* CCFM1052 and *Lactobacillus buchneri* CCFM1053 alone or in combination in adsorbing PFOA, relieving spleen atrophy caused by PFOA exposure, decreasing serum alanine transaminase (ALT) and γ-glutamyl transpeptidase (γ-GT) content after the PFOA exposure, relieving intestinal flora disorder after the PFOA exposure, decreasing abundance of *Allobaculum*, increasing abundance of Clostridiaceae, *Adlercreutzia, Bacteroides* and *Holdmania* in the intestinal tract, reducing occurrence of liver disease and metabolic diseases, relieving metabolic disorder of intestinal flora caused by PFOA exposure, increasing the content of acetic acid and butyric acid in the intestinal tract, improving fecal water content and decreasing first black stool defecation time of a patient with constipation, or preventing/treating constipation.

The present disclosure discloses a method for preparing a medicine, a health-care product and a functional food capable of relieving toxicity of PFOA, preventing and treating constipation, and preventing liver disease, hypertension and obesity by using lactobacilli. The method includes the following steps:
(1) culturing lactobacilli;
(2) collecting the lactobacilli or a metabolite thereof; and
(3) preparing the lactobacilli or the metabolite thereof into a medicine, a health-care product or a functional food; and
the lactobacilli is any one of following:
(a) *Lactobacillus fermentum* CCFM1051 has been deposited in Guangdong Microbial Culture Collection Center on Apr. 29, 2019 and has the preservation number of GDMCC No: 60649;
or (b) *Lactobacillus casei* CCFM1052 has been deposited in Guangdong Microbial Culture Collection Center on Apr. 29, 2019 and has the preservation number of GDMCC No: 60650; or
(c) *Lactobacillus buchneri* CCFM1053 has been deposited in Guangdong Microbial Culture Collection Center on Apr. 29, 2019 and has the preservation number of GDMCC No: 60651.

The present disclosure discloses 3 strains of lactobacilli with a PFOA adsorption capacity. The strains have high adsorption to PFOA and a potential to relieve PFOA-related metabolic diseases, and can be used to prepare a medicine or a health-care product for treating or relieving liver disease and metabolic diseases. The 3 strains of lactobacilli have the following biological characteristics:

1. *Lactobacillus fermentum* CCFM1051:
(1) bacterial characteristics: the bacteria are gram-positive, has globoid cells, has a diameter of 0.8-1.0 μm, and has no flagella or spores;
(2) colony characteristics: the colony has a milk white color and neat edges, is globoid, protruding, opaque and has a wet and smooth surface;
(3) growth properties: the lowest growth temperature of the strain is 15° C. and the highest growth temperature is 45° C.; the best growth temperature is 35-37° C.; the optimum growth pH is 6.5; and the strain enters a stationary phase after being cultured for 18 h;
(4) the bacteria have a good PFOA adsorption capacity in vitro;
(5) the bacteria have a good ability of scavenging 1,1-diphenyl-2-trinitrophenylhydrazine (DPPH) free radicals and hydroxyl radicals and a reducing ability in vitro;
(6) the *Lactobacillus fermentum* CCFM1051 can significantly relieve spleen atrophy in mice exposed to PFOA;
(7) the *Lactobacillus fermentum* CCFM1051 can significantly decrease serum IL-4 content in the mice exposed to PFOA;
(8) the *Lactobacillus fermentum* CCFM1051 can significantly decrease levels of serum alanine transaminase (ALT), aspartate aminotransferase (AST) and γ-glutamyl transpeptidase (γ-GT) content in the mice exposed to PFOA;
(9) the *Lactobacillus fermentum* CCFM1051 can significantly decrease abundance of S24-7 and *Lactobacillus*, increase abundance of *Bacteroides* and Eubacteriaceae in the intestinal tract of the mice exposed to PFOA, relieve intestinal disorder caused by PFOA exposure and reduce occurrence of liver disease, hypertension and obesity;
(10) the *Lactobacillus fermentum* CCFM1051 can significantly improve fecal water content and decrease first black stool defecation time in mice with constipation, and obviously relieve constipation of the mice; and
(11) the *Lactobacillus fermentum* CCFM1051 can significantly improve proliferation and MafA gene expression of INS-1 cells under high glucose and relieve PFOA-related diabetes.

2. *Lactobacillus casei* CCFM1052
(1) bacterial characteristics: the bacteria are gram-positive, has globoid cells, has a diameter of 0.8-1.0 μm, and has no flagella or spores;
(2) colony characteristics: the colony has a milk white color and neat edges, is globoid, protruding, opaque and has a wet and smooth surface;
(3) growth properties: the lowest growth temperature of the strain is 15° C. and the highest growth temperature is 45° C.; the best growth temperature is 35-37° C.; the optimum growth pH is 6.5; and the strain enters a stationary phase after being cultured for 18 h;
(4) the bacteria have a good PFOA adsorption capacity in vitro;
(5) the *Lactobacillus casei* CCFM1052 can significantly relieve spleen atrophy in mice exposed to PFOA;
(6) the *Lactobacillus casei* CCFM1052 can significantly decrease serum alanine transaminase (ALT) and γ-glutamyl transpeptidase (γ-GT) content in the mice exposed to PFOA;
(7) the *Lactobacillus casei* CCFM1052 can significantly decrease activity of superoxide dismutase (SOD) and content of malondialdehyde (MDA) in a liver homogenate of the mice exposed to PFOA;
(8) the *Lactobacillus casei* CCFM1052 can significantly decrease abundance of *Allobaculum*, increase abundance of Clostridiaceae, *Adlercreutzia, Bacteroides* and *Holdmania* in the intestinal tract of the mice exposed to PFOA, relieve intestinal disorder caused by PFOA exposure and reduce occurrence of liver disease and metabolic diseases;

(9) the *Lactobacillus casei* CCFM1052 can significantly increase the content of acetic acid and butyric acid in the intestinal tract of the mice exposed to PFOA and relieve metabolic disorder of intestinal flora caused by PFOA exposure;

(10) the *Lactobacillus casei* CCFM1052 can significantly improve fecal water content and decrease first black stool defecation time in mice with constipation; and

(11) the *Lactobacillus casei* CCFM1052 can significantly improve proliferation and MafA gene expression of INS-1 cells under high glucose and relieve PFOA-related diabetes.

3. *Lactobacillus buchneri* CCFM1053 has the following biological characteristics:
(1) bacterial characteristics: the bacteria are gram-positive, has globoid cells, has a diameter of 0.8-1.0 μm, and has no flagella or spores;
(2) colony characteristics: the colony has a milk white color and neat edges, is globoid, protruding, opaque and has a wet and smooth surface;
(3) growth properties: the lowest growth temperature of the strain is 15° C. and the highest growth temperature is 45° C.; the best growth temperature is 35-37° C.; the optimum growth pH is 6.5; and the strain enters a stationary phase after being cultured for 18 h;
(4) the bacteria have a good PFOA adsorption capacity in vitro;
(5) the *Lactobacillus buchneri* CCFM1053 can significantly relieve spleen atrophy in mice exposed to PFOA;
(6) the *Lactobacillus buchneri* CCFM1053 can significantly decrease levels of serum ALT, AST and γ-GT in the mice exposed to PFOA;
(7) the *Lactobacillus buchneri* CCFM1053 can significantly decrease levels of MDA and GSH in liver of the mice exposed to PFOA;
(8) the *Lactobacillus buchneri* CCFM1053 can significantly decrease serum TNF-α content in the mice exposed to PFOA;
(9) the *Lactobacillus buchneri* CCFM1053 can significantly decrease abundance of *Allobaculum*, increase abundance of *Bacteroides* and Eubacteriaceae in the intestinal tract of the mice exposed to PFOA, relieve intestinal disorder caused by PFOA exposure and reduce occurrence of liver disease;
(10) the *Lactobacillus buchneri* CCFM1053 can significantly improve fecal water content and decrease first black stool defecation time in mice with constipation, and relieve constipation of the mice; and
(11) the *Lactobacillus buchneri* CCFM1053 can significantly improve proliferation and MafA gene expression of INS-1 cells under high glucose and relieve PFOA-related diabetes.

Deposit of Biological Material

*Lactobacillus fermentum* CCFM1051 has been deposited in Guangdong Microbial Culture Collection Center on Apr. 29, 2019 and has the preservation number of GDMCC No: 60649.

*Lactobacillus casei* CCFM1052 has been deposited in Guangdong Microbial Culture Collection Center on Apr. 29, 2019 and has the preservation number of GDMCC No: 60650.

*Lactobacillus buchneri* CCFM1053 has been deposited in Guangdong Microbial Culture Collection Center on Apr. 29, 2019 and has the preservation number of GDMCC No: 60651.

DETAILED DESCRIPTION

Figure 1:
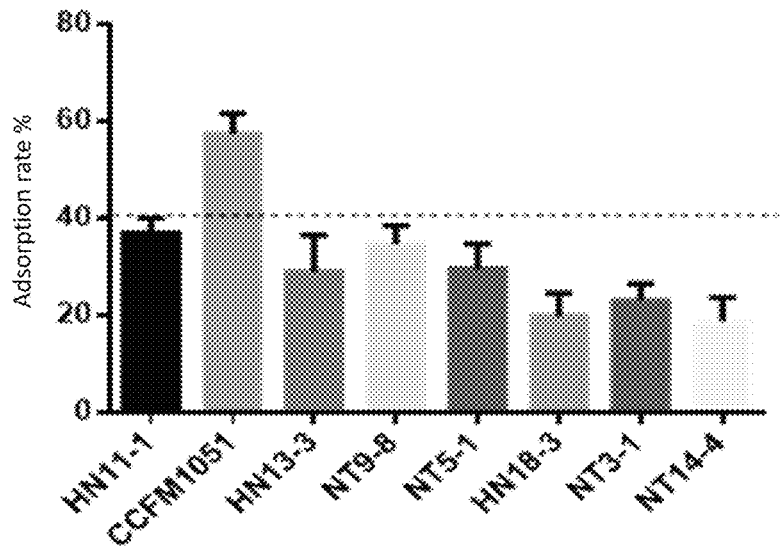
FIG. 1 is a schematic diagram of a concentration change of PFOA before and after adsorption, where after different lactobacilli were resuspended in vitro in a PFOA solution at a concentration of 10 mg/L and cultured at 37° C. in a shaker at 150 rpm for 6 h, an obtained sample solution passes through a 0.22 μm water filter membrane and enters an ultra-high performance liquid chromatography-mass spectrometer.

Example 1 Screening and Identification of *Lactobacillus fermentum* CCFM1051

(I) Separating and Screening of Lactobacilli:

(1) 1 g of fresh feces was taken from healthy adults; and the taken sample was enriched in an MRS medium containing sorbitol at 35° C. for 12 h;

(2) performing gradient dilution of the enriched samples, spreading the samples subjected to gradient dilution on MRS solid plates supplemented with 0.02% bromcresol purple, and performing culturing for 24-48 h;

(3) selecting single colonies with obvious color-changing zones and conforming to the basic morphology of lactobacilli, performing plate streaking purification, and screening and isolating lactobacilli;

(4) culturing the above single colonies in liquid MRS culture solutions for 24 h, then performing Gram staining, and selecting Gram-positive bacteria for performing subsequent experiments.

(II) Preliminary Identification of Lactobacilli: Calcium-Dissolving Zone Determination Method:

(1) culturing the lactobacilli screened in step (I) in a liquid sorbitol MRS culture solution for culturing the lactobacilli for 24 h, then taking 1 mL of the culture and centrifuging the culture at 8000 rpm for 2 min;

(2) the centrifuged culture was washed twice with a 0.05 M $KH_2PO_4$ solution;

(3) resuspending the obtained bacterial sludge, streaking the bacterial sludge on a sorbitol MRS-0.75% $CaCo_3$ solid medium, and culturing for 24 h;

(4) selecting colonies with obvious calcium-dissolving zones and being convex-round, fine and white without mycelia, and after Gram staining, preliminarily judging the bacteria as *Lactobacillus* if the bacterial cells were bacilliform as observed under microscope.

(III) Molecular Biological Identification of *Lactobacillus Fermentum*:

(1) a genome of single bacteria was extracted:

A. the lactobacilli screened out in step (II) were cultured overnight, 1 mL of a bacterial suspension cultured overnight was put into a 1.5 mL centrifuge tube and centrifuged for 2 min at 10,000 rpm, and bacteria were obtained after supernatant was discarded;

B. the bacteria were purged with 1 mL of sterile water and then centrifuged for 2 min at 10,000 rpm, and bacteria were obtained after supernatant was discarded;

C. 200 μL of SDS lysate was added for water bath for 30 min at 80° C.;

D. 200 μL of a phenol-chloroform solution was added to bacteria lysate, after bottom-up even mixing, centrifugation was performed for 5-10 min at 12,000 rpm, and 200 μL of supernatant was taken, where the phenol-chloroform solution had compositions of Tris-saturated phenol, chloroform and isoamyl alcohol according to a volume ratio of 25:24:1;

E. 400 μL of ice alcohol or ice isopropyl alcohol was added to 200 μL of supernatant to stand for 1 h at −20° C. and was then centrifuged for 5-10 min at 12,000 rpm, and supernatant was discarded;

F. 500 μL of 70% (volume percentage) ice alcohol was added for resuspending and precipitating and centrifuged for 1-3 min at 12,000 rpm, and supernatant was discarded;

G. drying was performed with an oven at 60° C., or air-drying was performed; and H. 50 μL of $ddH_2O$ was added for redissolving and precipitating for PCR; and (2) performing 16S rDNA PCR:

A. 50 μL PCR reaction system of 16S rDNA of bacteria: 10×Taq buffer, 5 μL; dNTP, 5 μL; 27F, 0.5 μL; 1492R, 0.5 μL; Taq enzyme, 0.5 μL; template, 0.5 μL; ddH$_2$O, 38 μL.

B. PCR conditions:

95° C., 5 min; 95° C., 10 s; 55° C., 30 s; 72° C., 30 s; steps 2-4, 30×; 72° C., 5 min; 12° C., 2 min;

(3) preparing a 1% agarose gel, then mixing the PCR product with 10× loading buffer, performing loading at a loading amount of 5 μL, performing running at 120 V for 30 min, and then performing gel imaging;

(4) the PCR product of 16S rDNA was sequenced and analyzed, an obtained sequence result was searched and subjected to a similarity comparison in GeneBank by using BLAST, a sequencing result was selected and identified as a newly discovered strain belonging to *Lactobacillus fermentum*, and the strain was stored at −80° C. for later use.

Example 2 PFOA-Adsorbing Ability of Different Lactobacilli In Vitro

The *Lactobacillus fermentum* CCFM1051 and control strains were purified and activated, inoculated in an MRS liquid medium at an inoculation quantity of 1% (v/v), and cultured at 37° C. for 18 h. The bacteria were collected by centrifugation at 8,000 r/min for 5 min, a precipitate was cleaned with normal saline and centrifuged at 8,000 r/min for 5 min, and the precipitate was taken to obtain live bacterial cells, that is, wet bacteria. The wet bacteria were resuspended in a 10 mg/L PFOA solution, and the final bacteria concentration reached 1 g Dry bacteria/L. As a blank control, wet bacteria were resuspended in ultrapure water without PFOA. A 0.1 M NaOH or HCl solution was used to quickly adjust a pH of the PFOA solution containing the bacterial solution to 3.0, where an ionic strength of a small amount of NaOH or HCl (less than 0.5 ml) has a negligible effect on PFOA adsorption. Subsequently, a 250-ml conical flask containing 100 ml of an obtained sample solution was placed in a shaker at 37° C. and 150 rpm for cultivation, a sample was taken for determination after 6 h, and an average value of 2 parallel tests was taken.

Determination of PFOA adsorption quantity: after the adsorption experiment, the sample solution was centrifuged at 8,000 r/min for 5 min and filtered with a 0.22 μm water membrane, a concentration of PFOA was determined by using UPLC-MS of a Waters SYNAPT MS system via an Acquity UPLC BEH c18 column (2.1×100 mm, 1.7 μm, Waters Co.) and at a column temperature of 35° C. and an injection volume of 1 μL. Gradient elution was conducted by using a 100% (v/v) acetonitrile solution (a solution A) and a 0.1% (v/v) formic acid aqueous solution (a solution B) as eluents at a flow rate of 0.3 mL/min.

TABLE 1

| Gradient elution condition | | | | |
|---|---|---|---|---|
| | t/min | | | |
| | 0-0.5 | 0.5-5.0 | 5.0-7.0 | 7.0-7.5 |
| Ratio of solution A | 70% | 70-100% | 100% | 100-70% |

Mass spectrometry conditions: ionization source: ESI source; MRM detection; MS+detection; Capillary; 3.0 kV; Conc: 40.00 V; Source Temperature: 120° C.; Desolvation Temperature: 400° C.; Conc Gas Flow: 50 L/h; Desolvation Gas Flow: 700 L/h. Gas flow rate: 0.1 ml/min; proton ratio scanning range: 100-2,000; and scanning time: 1 s and interval: 0.061 s. The results were analyzed by MassLynxV4.1 (Waters Company); and the adsorption quantity of PFOA by lactobacilli was calculated according to difference of the PFOA concentration before and after adsorption. The determination results were shown in FIG. 1. The adsorption quantity of 10 mg/L PFOA by the CCFM1051 was 57.5%±1.5% and the adsorption quantity of the PFOA by other *Lactobacillus fermentum* was less than 40%.

Example 3 Good Ability of Scavenging 1,1-diphenyl-2-trinitrophenylhydrazine (DPPH) Free Radicals and Hydroxyl Radicals and Reducing Ability In Vitro 1 mL of complete *lactobacillus* cell suspension was fully mixed with 1 mL of a freshly prepared DPPH anhydrous ethanol solution (0.2 mmol/L), and reaction was conducted at 37° C. for 30 min in a dark place. DPPH was mixed with PBS (pH 7.2) as a control sample and incubated under the same condition. After centrifugation at 7,000×g for 10 min, an absorbance was measured at 517 nm and the ability of the lactobacilli to scavenge DPPH free radicals was calculated according to the following formula:

$$\text{DPPH free radical-scavenging rate (\%)} = [1 - A_{517}(\text{sample})/A_{517}(\text{control})] \times 100\%.$$

1 mL of 1,10-phenanthroline, 1 mL of PBS (pH 7.2), 1 mL of the complete *lactobacillus* cell suspension and 1 mL of FeSO$_4$ were mixed evenly as a mixture 1. 1 mL of H$_2$O$_2$ was added to the mixture 1, water bath was conducted at 37° C. for 1.5 h, and the absorbance was measured at 536 nm and presented as A$_{536}$ (sample). The complete *lactobacillus* cell suspension in the mixture 1 was replaced with the same volume of distilled water, culture was conducted under the same condition, measurement was conducted and the result was represented as A$_{536}$ (blank). The H$_2$O$_2$ added to the mixture 1 was replaced with the same volume of distilled water, culture was conducted under the same condition, measurement was conducted and the result was represented as A$_{536}$ (control). The ability of the lactobacilli to scavenge hydroxyl radicals was calculated according to the following formula:

$$\text{Hydroxyl radical-scavenging rate (\%)} = [A_{536}(\text{sample}) - A_{536}(\text{blank})] / [A_{536}(\text{control}) - A_{536}(\text{blank})] \times 100\%.$$

Figure 2:
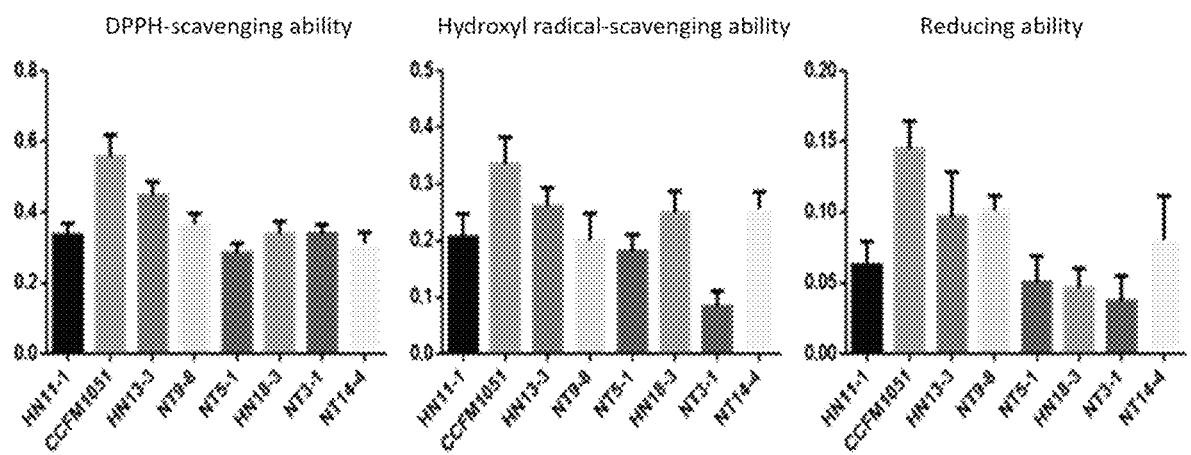
FIG. 2 shows 1,1-diphenyl-2-trinitrophenylhydrazine (DPPH) free radical and hydroxyl radical-scavenging ability and reducing ability of the different lactobacilli in vitro.

0.5 mL of the complete *lactobacillus* cell suspension was mixed with the same volume of potassium ferricyanide (1%) and PBS buffer (pH 6.6), and shaking was conducted to make the system uniform. Distilled water was mixed with the potassium ferricyanide and PBS as a blank control. The mixed system was cultured at 50° C. for 20 min and rapidly cooled, and 0.5 mL of 10% trichloroacetic acid was added. After centrifugation at 2,000×g for 5 min, 1 mL of a supernatant was mixed with 1 mL of 0.1% ferric chloride and reaction was conducted for 10 min. Absorbance was measured at 700 nm and cysteine was used as a standard to characterize reducing power. The results were shown in FIG. 2. The DPPH-scavenging ability of the CCFM1051 was 57±4.2%, the DPPH-scavenging ability of other lactobacilli was less than 50%, the hydroxyl radical-scavenging ability of the CCFM1051 was 32±4.5%, while the hydroxyl radical-scavenging ability of other lactobacilli was less than 30%, the reducing ability of the CCFM1051 was 14±1.8%, and the reducing ability of other lactobacilli was less than 13%.

Example 4 The *Lactobacillus fermentum* CCFM1051 can Significantly Relieve Spleen Atrophy in Mice Exposed to PFOA 50 6-week-old male C57BL/6J mice were selected. After one week of adaptation to the environment, the mice were randomly divided into five groups according to body weight: a control group, a model group, a fluoxetine intervention group, and a *Lactobacillus fermentum* CCFM1051 intervention group, LGG intervention group, each containing 10 mice. Animal grouping and treatment methods are shown in Table 2.

TABLE 2

Grouping and treatment methods of animal experiment

| Groups | Treatment method | Experimental Period |
|---|---|---|
| Control group | Continuously gavaged with 200 µL of a 3% sucrose solution for 11 days | 11 days |
| Model group | Continuously gavaged with 200 µL of a 3% sucrose solution for 10 days and gavaged with 3 g of PFOA/kgBW/200 µL/mouse on the 11$^{th}$ day | 11 days |
| Quercetin intervention group | Continuously gavaged with 200 µL of a 3 g/L quercetin solution for 10 days and gavaged with 3 g of PFOA/kgBW/200 µL/mouse on the 11$^{th}$ day | 11 days |
| *Lactobacillus fermentum* CCFM1051 intervention group | Continuously gavaged with the strain CCFM1051 (1 × 10$^9$ cfu/200 µL/mouse/day) for 10 days and gavaged with 3 g of PFOA/kgBW/200 µL/mouse on the 11$^{th}$ day | 11 days |
| LGG intervention group | Continuously gavaged with strain LGG (1 × 10$^9$ cfu/200 µL/mouse/day) for 10 days and gavaged with 3 g of PFOA/kgBW/200 µL/mouse on the 11$^{th}$ day | 11 days |

The mice were weighed on the 13$^{th}$ day and euthanized. The spleen was taken out and weighed in a wet state to calculate an organ coefficient. The organ coefficient of the mouse spleen was calculated according to the following formula:

Spleen organ coefficient=wet weight of spleen/ weight of mice before euthanasia.

Figure 3:
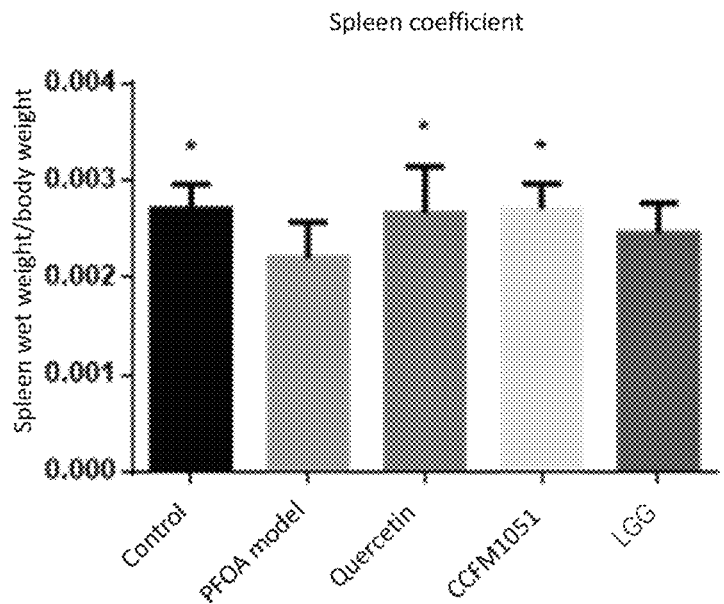
FIG. 3 is a diagram showing a change of a spleen ratio of mice exposed to PFOA after 10 days of intervention with different substances, where *P<0.05 (vs a model group).

The results were shown in FIG. 3. The *Lactobacillus fermentum* CCFM1051 can significantly reverse the spleen atrophy of the mice caused by PFOA exposure and had an effect better than that of naringenin.

Figure 4:
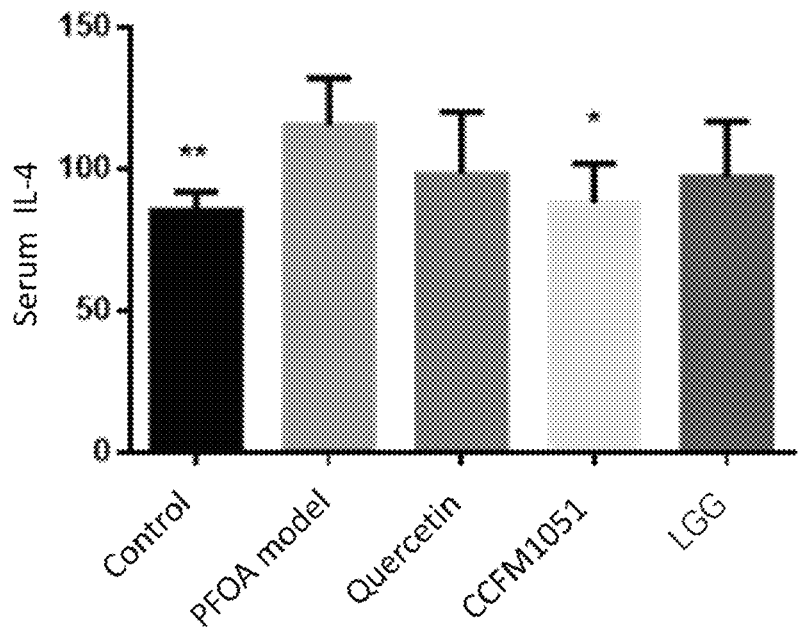
FIG. 4 is a schematic diagram showing serum interleukin-4 (IL-4) in the mice exposed to PFOA after 10 days of intervention with different substances, where *P<0.05 and **P<0.01 (vs the model group).

Example 5 The *Lactobacillus fermentum* CCFM1051 can Significantly Decrease Serum IL-4 Content in the Mice Exposed to PFOA The mice in example 4 were euthanized on the 13$^{th}$ day. Serum was collected and centrifuged at 3,000 g for 15 min, and the content of IL-4 in the serum was detected by an ELISA kit. The results showed that the *Lactobacillus fermentum* CCFM1051 can significantly relieve an immune damage of mice caused by PFOA exposure (FIG. 4) and restore the serum IL-4 content to a normal level, and had an effect better than quercetin.

Figure 5:
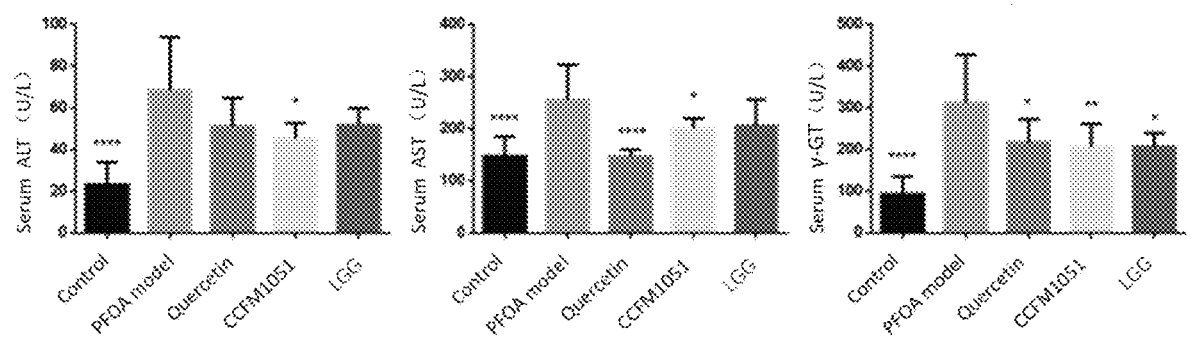
FIG. 5 is a schematic diagram of levels of serum ALT, AST and γ-GT in the mice exposed to PFOA after 10 days of intervention with different substances, where *P<0.05, P<0.01, *P<0.001 and ****P<0.0001 (vs the model group).

Example 6 The *Lactobacillus fermentum* CCFM1051 can Significantly Decrease Serum Alanine Transaminase (ALT), Aspartate Aminotransferase (AST) and γ-Glutamyl Transpeptidase (γ-GT) Levels in the Mice Exposed to PFOA The serum in the example 5 was taken and serum alanine transaminase (ALT), aspartate aminotransferase (AST) and γ-glutamyl transpeptidase (γ-GT) levels were detected by using a fully automatic biochemical analyzer. ALT mainly existed in a soluble part of hepatocyte protoplasm and an increase of ALT activity indicated that hepatocytes were destroyed and cell membrane permeability was enhanced. AST mainly existed in mitochondria of hepatocytes and an increase of AST activity indicated a mitochondrial damage. Results were shown in FIG. 5 that the *Lactobacillus fermentum* CCFM1051 can significantly decrease serum ALT, AST and γ-GT content in the mice exposed to PFOA. The results indicated that the *Lactobacillus fermentum* CCFM1051 can significantly relieve damages of mouse hepatocyte membrane structure and functions caused by PFOA, decrease ALT from 68.8±15.2 U/L in the PFOA model group to 44.5±12.4 U/L, decrease AST from 240.7±48.2 U/L in the PFOA model group to 208.6±13.4 U/L and decrease γ-GT from 310.5±80.3 U/L in the PFOA model group to 215±15.4 U/L.

Figure 6:
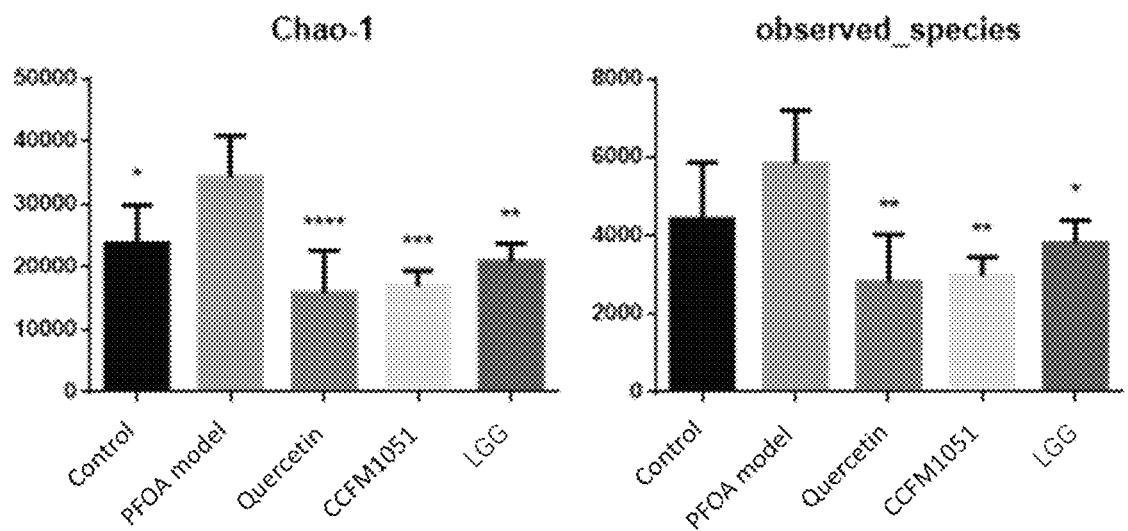
FIG. 6 is a schematic diagram of changes of the α diversity of the intestinal flora of the mice exposed to PFOA after 10 days of intervention with different substances, where *P<0.05, P<0.01 and *P<0.001 (vs the model group).

Example 7 The *Lactobacillus fermentum* CCFM1051 can Significantly Decrease Abundance of S24-7 and *Lactobacillus*, Increase Abundance of *Bacteroides* and Eubacteriaceae in the Intestinal Tract of the Mice Exposed to PFOA, Relieve Intestinal Disorder Caused by PFOA Exposure and Reduce Occurrence of Liver Disease, Hypertension and Obesity The fresh feces of the mice on the 12$^{th}$ day in example 4 were taken and the total DNA in the mouse feces sample was extracted by using an MP feces kit. The specific operation steps were as follows mainly referring to the kit instructions. Mouse feces genome was used as a template, a forward primer 520F (5'-AYTGGGYDTAAAGNG-3', SEQ ID NO. 1) and a reverse primer 802R (5'-TACNVGGGTATCTAATCC-3', SEQ ID NO. 2) were used for amplifying V3-V4 region fragments of 16S rDNA and a target fragment had a length about 247 bp. After a PCR reaction was over, all the PCR samples with observed target bands were subjected to electrophoresis again, a 2.0% agarose gel was prepared, electrophoresis was conducted at 120 V for 40 min, and after gel running, the target bands were quickly cut under UV light. The target band gel was recovered according to instructions of a QIAquick gel extraction kit. The DNA concentration of the samples was detected according to a Qubit DNA3.0 kit, a library was constructed according to a TurSeq DNA LT sample preparation kit and its instructions, and determination was conducted by an Illumina Miseq sequencer according to an MiSeq regent kit and its instructions. After the sequencing, sequences with a length <200 bp, primer sequences, and single sequences that cannot be spliced were removed, and standard splicing sequences with overlapping bases>10 bp and no mismatches were used. Sequences with a similarity greater than 97% were defined as an operational taxonomic unit (OTU) and species was determined by the Ribosomal Database Project (RDP) Naïve Bayesclassifier. The α-diversity and β-diversity of the samples were calculated to evaluate the bacterial diversity of the samples. The α-diversity was characterized by indexes of chao1 and observed species. The results were shown in FIG. 6 that the α-diversity of the intestinal flora of the mice in the PFOA model group was increased, indicating that PFOA exposure would be accompanied by a certain degree of intestinal disorder. The *Lactobacillus fermentum* CCFM1051 can significantly decrease the α-diversity of the intestinal flora and relieve intestinal disorder.

Figure 7:
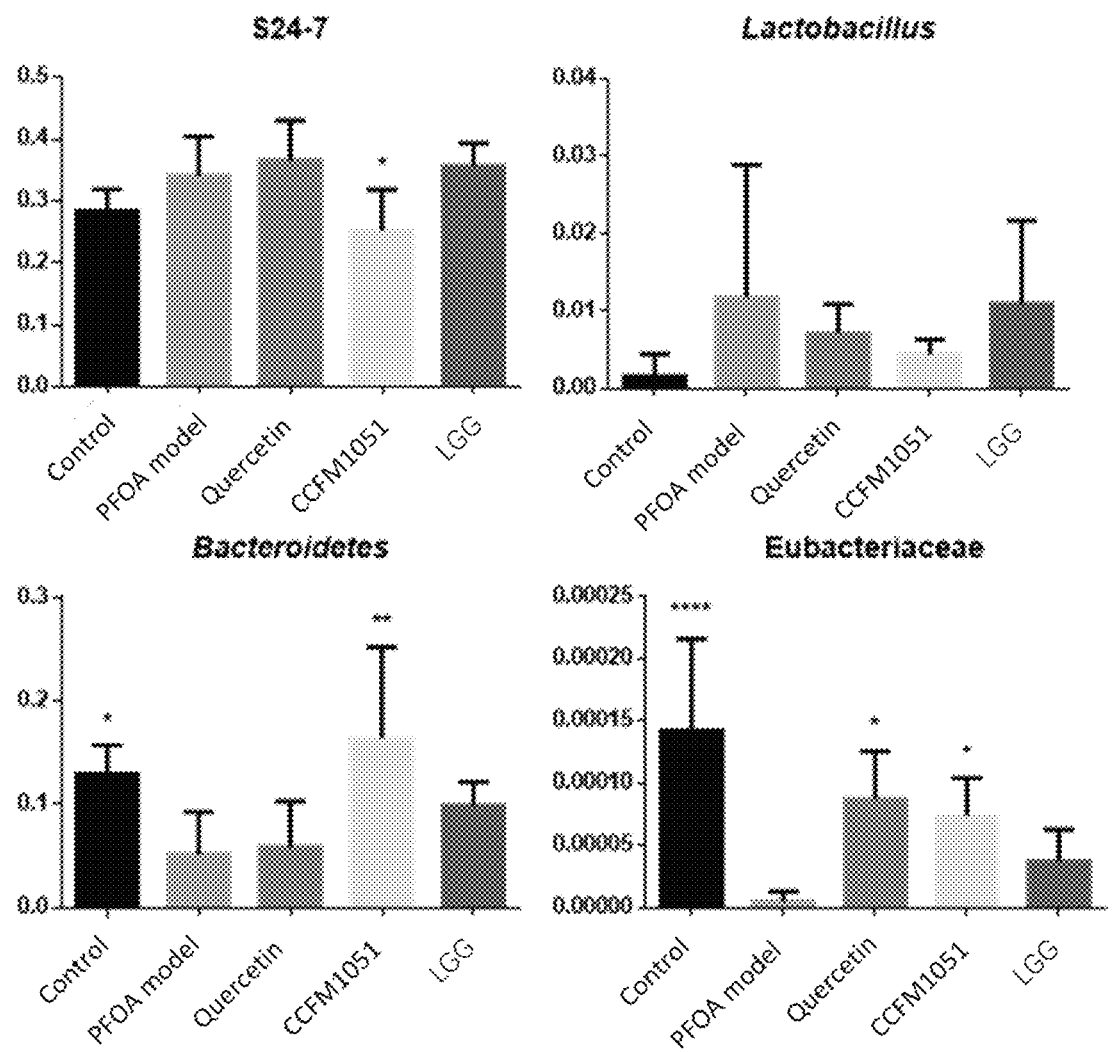
FIG. 7 is a schematic diagram of changes of abundance of S24-7, *Lactobacillus, Bacteroides* and Eubacteriaceae in the intestinal tract of the mice exposed to PFOA after 10 days of intervention with different substances, where *P<0.05 and **P<0.01 (vs the model group).

In addition, the abundance of S24-7 and *lactobacillus* was significantly increased in the mice exposed to PFOA, but the *Lactobacillus fermentum* CCFM1051 can significantly reverse the increase; S24-7 was highly localized in the gastrointestinal tract of homothermal animals and the gram-negative non-motile anaerobic microorganisms can ferment a variety of carbohydrates and were related with occurrence and development of non-alcoholic fatty liver disease and hypertension. *Lactobacillus* is a common probiotic in the normal gastrointestinal tract and urogenital organs. The abundance of the *lactobacillus* was increased in the PFOA model group and an exposure model in a *lactobacillus* prevention experiment, indicating that the *lactobacillus* may be subjected to feedback adjustment after PFOA exposure. The *Lactobacillus fermentum* CCFM1051 can also significantly increase the abundance of *Bacteroides* and Eubacteriaceae in the mice exposed to PFOA (FIG. 7). The *Bacteroides*, also known as bacaeroides, belongs to bacteroidaceae and is gram-negative, spore-free and specific anaerobic bacteria. The *Bacteroides* normally inhabits the intestines, mouth, upper respiratory tract and reproductive tract of humans and animals. The *Bacteroides* is a large number of normal flora in humans and animals, accounting for more than ¼ of the intestinal flora of an adult individual. The *Bacteroides* is a nutrient source for gut bacteria, regulates expressions of a variety of host genes, including those involved in nutrient absorption, mucosal barrier strengthening, and angiogenic factor production, activates T cell-dependent immune responses, affects expressions of Paneth cell proteins and restricts colonization of pathogens in the gastrointestinal tract. The Eubacteriaceae is associated with hepatic encephalopathy, that is restoration of a dysfunctional gut-liver-brain axis in cirrhosis, and abundance of the eubacteriaceae is significantly reduced after biliary-gut bypass in a severely obese patient. The above results indicated that the *Lactobacillus fermentum* CCFM1051 relieved toxicity of PFOA and was also capable of regulating intestinal flora, immunity and intestinal barrier, and reducing occurrence of liver disease, hypertension and obesity.

Example 8 The *Lactobacillus fermentum* CCFM1051 can Relieve Constipation of Mice 40 SPF male BALB/c mice (20-25 g) were randomly divided into 5 groups: a blank control group, a constipation model control group, a *Lactobacillus fermentum* CCFM1051 intervention group, a *Lactobacillus plantarum* control group and a phenolphthalein treatment group with 10 mice in each group.

The freeze-dried *Lactobacillus fermentum* CCFM1051 powder was resuspended in skim milk powder to prepare a bacterial suspension with a concentration of $4.0 \times 10^9$ CFU/mL. 14 days before an experiment, the mice in the intervention group were gavaged with 0.25 mL of the *Lactobacillus fermentum* CCFM1051 skim milk suspension ($4.0 \times 10^9$ CFU/mL) every day, the mice in the *Lactobacillus plantarum* group were gavaged with an equal amount of *L. plantarum* ST-III and the mice in the other 3 groups were gavaged with an equal amount of bacteria-free skim milk. On the $15^{th}$ to $17^{th}$ day of the experiment, the mice in the negative control group were gavaged with 0.25 mL of normal saline and the mice in the other four groups were gavaged with 0.25 mL of a loperamide solution at 1 mg/mL to ensure that the gavage amount of loperamide in the mice was 10 mg/kgBW.

One hour after the gavage, the mice in the negative control group and the constipation model control group were gavaged with skim milk, the mice in the *Lactobacillus fermentum* CCFM1051 intervention group was gavaged with 0.25 mL of *Lactobacillus fermentum* CCFM1051 ($4.0 \times 10^9$ CFU/mL), and the mice in the phenolphthalein treatment control group was gavaged with 0.25 mL of a phenolphthalein solution at 7 mg/mL to ensure that the gavage amount of phenolphthalein in the mice was 70 mg/kgBW. The mice in the *Lactobacillus plantarum* group were gavaged with 0.25 mL of *L. plantarum* ST-III ($4.0 \times 10^9$ CFU/mL).

The mouse feces were collected every day during the period for determining the fecal water content of the mice. The fecal water content was calculated by using the following formula:

Fecal water content (%)=(wet weight of feces−dry weight of feces)/wet weight of feces×100.

Figure 8:
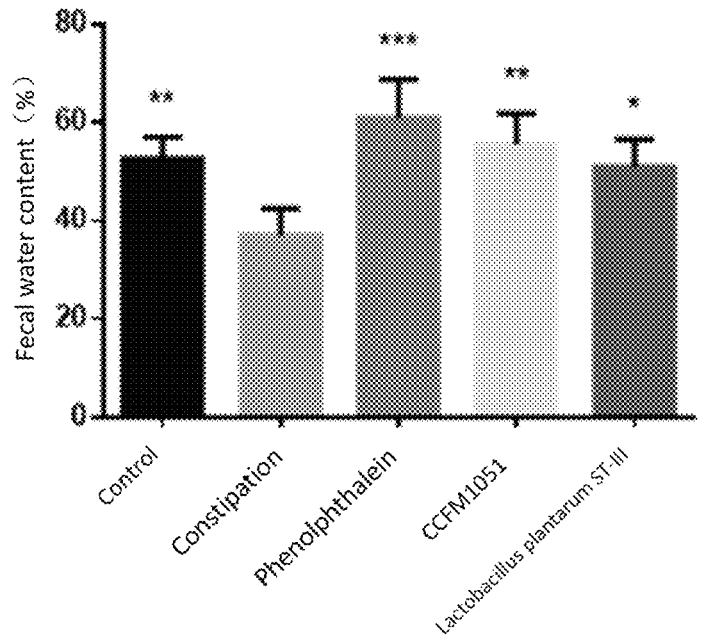
FIG. 8 shows improvement of fecal water content in mice with constipation after intervention with different substances, where *P<0.05, P<0.01 and *P<0.001 (vs the model group).
Figure 9:
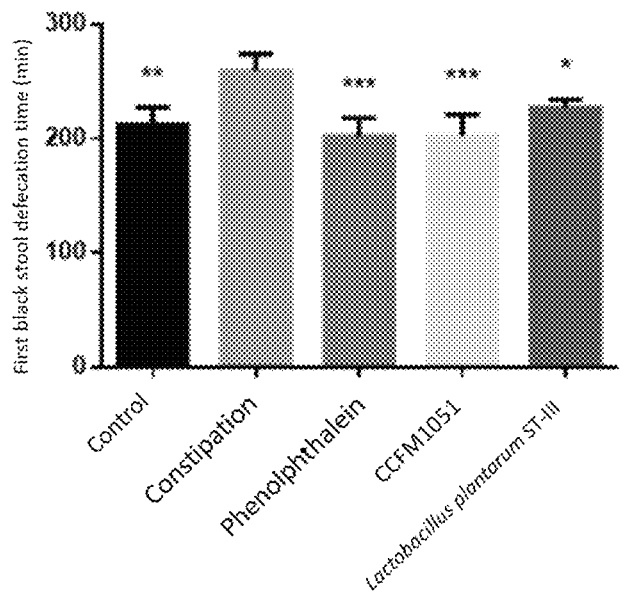
FIG. 9 shows decrease of first black stool defecation time in the mice with constipation after intervention with different substances, where *P<0.05, P<0.01 and *P<0.001 (vs the model group).

On the morning of the $17^{th}$ day, the mice in the blank control group were gavaged with normal saline, the mice in the other groups were gavaged with loperamide, after the gavage for 1 h, all the mice were gavaged with 0.25 mL of an activated carbon arabic gum aqueous solution, each mouse was separately placed in a clean stainless steel cage covered with absorbent paper, time (min) from start of the gavage with the activated carbon to defecation of first black stool was recorded as first black stool defecation time to evaluate an effect of the *Lactobacillus fermentum* CCFM1051 on constipation of the mice, and during the period, the mice ate and drank freely. The results were shown in FIG. 8 and FIG. 9. As shown in FIG. 8, the *Lactobacillus fermentum* CCFM1051 can relieve constipation, increase the fecal water content and shorten the first black stool defecation time, and had an effect better than that of *Lactobacillus plantarum* ST-III.

Example 9 The *Lactobacillus fermentum* CCFM1051 can Promote Proliferation and MafA mRNA Expression of High Glucose-Induced INS-1 Cells In an experiment, 5 groups were divided: a normal group (a normal culture solution containing 11.1 mmol/L of glucose), a high glucose group (a high glucose culture solution containing 22.2 mmol/L of glucose), a rosiglitazone group (a high glucose culture solution+80 μmol/L of rosiglitazone), a CCFM1051 group (a high glucose culture solution+$1 \times 10^9$ CFU/mL of a CCFM1051 bacterial solution) and an LGG group (a high glucose culture solution+1×10$^9$ CFU/mL of a LGG bacterial solution).

INS-1 cells (code: BH-AC0530) were inoculated in a RPMI-1640 culture solution (containing 11.1 mmol/L of glucose, 10% of FBS, 50 μmol/L of 2-mercaptoethanol, 1 mmol/L of pyruvic acid and 10 mmol/L of HEPES) and cultured at 37° C. in a 5% CO$_2$ incubator.

Determination of cell proliferation by a CCK-8 assay: the cells in a good state were digested and centrifuged, the treated cells were inoculated on a 96-well plate with about 5×10$^3$ cells in each well, no cells were inoculated into peripheral wells of the plate to prevent an edge effect, and a PBS solution was added at the same time. After the cells adhered to walls, a RPMI-1640 medium containing 0.5% fetal bovine serum was added to each well, and a synchronized treatment was conducted for 24 h. At the end of the synchronization, corresponding medium was added into each well according to the grouping, culture was conducted for 48 h, three duplicate wells were arranged in each group and a zero-adjustment well was arranged. After drug intervention, an old medium was aspirated, the cells were washed twice with PBS, 180 μL of a serum-free medium and 20 μL of a CCK-8 solution were added, and the cells were incubated for 3-4 h. After the incubation, the absorbance of each well was measured at 450 nm by using a microplate reader.

Determination of MafA mRNA expression: RNA was extracted by a Trizol method, an original culture solution in a 6-well plate was discarded, the cells were washed twice with pre-cooled PBS, the cells were lysed by adding 1.0 mL of Trizol in each well, a lysate containing the cells was transferred to an enzyme-free EP tube, the lysate was pipetted until there was no obvious precipitate and standing was conducted for 5 min. 0.2 mL of chloroform was added to each EP tube, vigorous shaking was conducted for 15 s, and an obtained solution was placed at a room temperature for 2-3 min. The obtained solution was centrifuged at 12,000 rpm for 15 min at 4° C., about 0.4 mL of a supernatant was aspirated and transferred to another enzyme-free EP tube, 0.5 mL of isopropanol was added, an obtained mixture was inverted and mixed uniformly, and standing was conducted at a room temperature for 10 min. The standing solution was centrifuged at 12,000 rpm for 10 min at 4° C., a supernatant was discarded carefully, 1.0 mL of 75% ethanol was added and an obtained mixture was inverted and mixed uniformly. The obtained mixture was centrifuged at 12,000 rpm for 5 min at 4° C., a supernatant was discarded, and drying was conducted at a room temperature for 2-5 min. 20 μL of DEPC-treated water was added for dissolving and an obtained product was stored at 80° C. for standby use. The concentration and mass of RNA were determined and a reverse transcription was conducted according to the instructions of a reverse transcription kit. A cDNA obtained by the reverse transcription was detected by qRT-PCR, where MafA specific primers were as follows: F: 5'-atcactctgcc-caccatcac-3' (SEQ ID NO. 3) and R: 5'-atgacctcctccttgctgaa-3' (SEQ ID NO. 4). PCR system: F (10 μM), 0.50 μL; R (10 μM), 0.50 μL; cDNA template, 1.00 μL; dd H$_2$O, 3.00 μL; and mix, 5.00 μL. PCR program was as follows: 95° C., 2 min;

(95° C., 30 sec; 60° C., 30 sec; 72° C., 20 sec)×35; and 72° C., 5 min; and after the target gene was detected by real-time PCR, the relative gene expression was analyzed by a $2^{-\Delta\Delta CT}$ method. An expression level of a target gene in the INS-1 cells of each group of rats was analyzed by using a CFX Manager software, the expression level of the normal group was taken as 1, and compared with the normal group, the gene expression levels of other groups were calculated.

Figure 10:
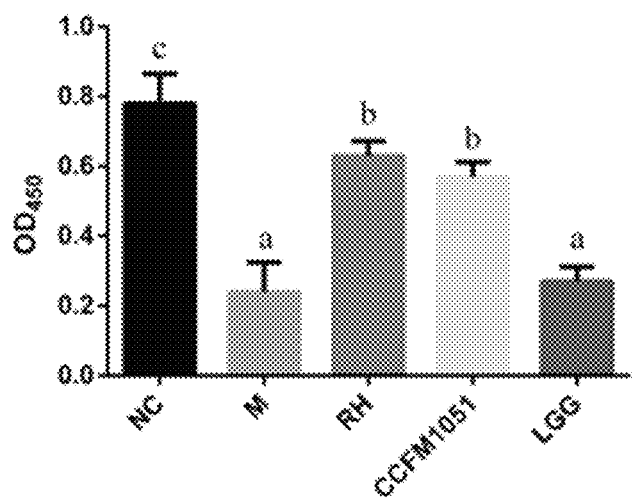
FIG. 10 shows effects of different strains on proliferation of INS-1 cells under high glucose.

The results of the CCK-8 assay were shown in FIG. 10. Compared with the normal group, the cell growth in the high glucose group was significantly decreased (P<0.05); the cell proliferation in the rosiglitazone control group was significantly increased compared with that in the high glucose group (P<0.05); and the cell proliferation in the CCFM1051 group was also significantly increased compared with that in the high glucose group (P<0.05).

Figure 11:
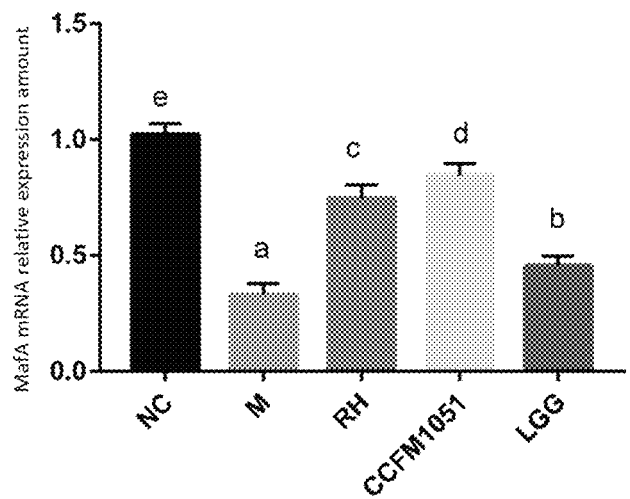
FIG. 11 shows effects of different strains on MafA gene expression of INS-1 cells under high glucose.

The expression of MafA mRNA was shown in FIG. 11. The expression of the MafA mRNA in the high glucose group was significantly lower than that in the normal group (P<0.05), while the expression of the MafA mRNA in the rosiglitazone positive control group and CCFM1051 group was significantly increased compared with that in the high glucose group (both P<0.05).

Example 10 Preparation of Fermented Food by Using *Lactobacillus fermentum* CCFM1051

(1) Preparation of Fruit and Vegetable Drink

Fresh vegetables were washed and juiced, and the juice was subjected to high-temperature instant sterilization. After high-temperature sterilization was performed at 140° C. for 2 s, the temperature was immediately reduced to 37° C., and the juice was inoculated with a *Lactobacillus fermentum* CCFM1051 bacterial starter prepared by the disclosure to make the concentration reach 10$^6$ CFU/mL or above, and was stored under refrigeration at 4° C., thereby obtaining a fruit and vegetable beverage containing the live *B. breve* CCFM1051 of the disclosure. The fruit and vegetable product included cucumber, carrot, beet, celery and cabbage products.

(2) Preparation of Fermented Dairy Product

The *Lactobacillus fermentum* CCFM1051 was inoculated into raw materials of a dairy product or a bean product to prepare a fermented dairy product or a fermented bean product; and the dairy product included milk, sour cream and cheese.

(3) The *Lactobacillus fermentum* CCFM1051 was inoculated into solid, semi-solid or liquid raw materials for fermentation to prepare a solid fermented food, a liquid fermented food and a semi-solid fermented food.

Similar to a use effect of the *Lactobacillus fermentum* CCFM1051, the fermented food prepared from the CCFM1051 can significantly relieve spleen atrophy caused by PFOA exposure, significantly decrease serum IL-4 content of mice exposed to PFOA, significantly increase serum ALT, AST and γ-GT of the mice exposed to PFOA, relieve intestinal flora disorder of the mice exposed to PFOA, decrease abundance of S24-7 and *Lactobacillus*, increase abundance of *Bacteroides* and Eubacteriaceae in the intestinal tract, normalize the intestinal flora and reduce occurrence of liver disease, hypertension and obesity. The fermented food containing the *Lactobacillus fermentum* CCFM1051 can significantly improve fecal water content and decrease first black stool defecation time in mice with constipation, and obviously relieve constipation of the mice. A cell experiment showed that the fermented food containing the *Lactobacillus fermentum* CCFM1051 can significantly improve proliferation and MafA gene expression of INS-1 cells under high glucose and relieve PFOA-related diabetes. An in-vitro experiment showed that the *Lactobacillus fermentum* CCFM1051 can well adsorb PFOA, effectively scavenge 1,1-diphenyl-2-trinitrophenylhydrazine (DPPH) free radicals and hydroxyl radicals and present a good reducing ability.

The probiotics with high adsorption capacity to PFOA and high antioxidant ability and not colonized in humans were screened out, can inhibit an oxidative stress caused by the PFOA, and can also fundamentally remove the PFOA in humans. The *Lactobacillus fermentum* CCFM1051 can be used to prepare a food, a health-care product and a medicine capable of relieving toxicity of PFOA, and has a very broad use prospect.

Example 11 Screening and Identification of *Lactobacillus casei* CCFM1052

(I) Separating and Screening of Lactobacilli:

(1) 1 g of fresh feces was taken from healthy adults; and the taken sample was enriched in an MRS medium containing sorbitol at 35° C. for 12 h;

(2) performing gradient dilution of the enriched samples, spreading the samples subjected to gradient dilution on MRS solid plates supplemented with 0.02% bromcresol purple, and performing culturing for 24-48 h;

(3) selecting single colonies with obvious color-changing zones and conforming to the basic morphology of lactobacilli, performing plate streaking purification, and screening and isolating lactobacilli;

(4) culturing the above single colonies in liquid MRS culture solutions for 24 h, then performing Gram staining, and selecting Gram-positive bacteria for performing subsequent experiments.

(II) Preliminary Identification of Lactobacilli: Calcium-Dissolving Zone Determination Method:

(1) culturing the lactobacilli screened in step (I) in a liquid sorbitol MRS culture solution for culturing the lactobacilli for 24 h, then taking 1 mL of the culture and centrifuging the culture at 8000 rpm for 2 min;

(2) the centrifuged culture was washed twice with a 0.05 M $KH_2PO_4$ solution;

(3) resuspending the obtained bacterial sludge, streaking the bacterial sludge on a sorbitol MRS-0.75% $CaCO_3$ solid medium, and culturing for 24 h;

(4) selecting colonies with obvious calcium-dissolving zones and being convex-round, fine and white without mycelia, and after Gram staining, preliminarily judging the bacteria as *Lactobacillus* if the bacterial cells were bacilliform as observed under microscope.

(III) Molecular Biological Identification of *Lactobacillus casei*:

(1) a genome of single bacteria was extracted:

A. the lactobacilli screened out in step (II) were cultured overnight, 1 mL of a bacterial suspension cultured overnight was put into a 1.5 mL centrifuge tube and centrifuged for 2 min at 10,000 rpm, and bacteria were obtained after supernatant was discarded;

B. the bacteria were purged with 1 mL of sterile water and then centrifuged for 2 min at 10,000 rpm, and bacteria were obtained after supernatant was discarded;

C. 200 µL of SDS lysate was added for water bath for 30 min at 80° C.;

D. 200 µL of a phenol-chloroform solution was added to bacteria lysate, after bottom-up even mixing, centrifugation was performed for 5-10 min at 12,000 rpm, and 200 µL of supernatant was taken, where the phenol-chloroform solution had compositions of Tris-saturated phenol, chloroform and isoamyl alcohol according to a volume ratio of 25:24:1;

E. 400 µL of ice alcohol or ice isopropyl alcohol was added to 200 µL of supernatant to stand for 1 h at −20° C. and was then centrifuged for 5-10 min at 12,000 rpm, and supernatant was discarded;

F. 500 µL of 70% (volume percentage) ice alcohol was added for resuspending and precipitating and centrifuged for 1-3 min at 12,000 rpm, and supernatant was discarded;

G. drying was performed with an oven at 60° C., or air-drying was performed; and H. 50 µL of $ddH_2O$ was added for redissolving and precipitating for PCR; and (2) performing 16S rDNA PCR:

A. 50 µL PCR reaction system of 16S rDNA of bacteria:

10×Taq buffer, 5 µL; dNTP, 5 µL; 27F, 0.5 µL; 1492R, 0.5 µL; Taq enzyme, 0.5 µL; template, 0.5 µL; $ddH_2O$, 38 µL.

B. PCR conditions:

95° C., 5 min; 95° C., 10 s; 55° C., 30 s; 72° C., 30 s; steps 2-4, 30×; 72° C., 5 min; 12° C., 2 min;

(3) preparing a 1% agarose gel, then mixing the PCR product with 10× loading buffer, performing loading at a loading amount of 5 µL, performing running at 120 V for 30 min, and then performing gel imaging;

(4) a PCR product of 16S rDNA was subjected to sequencing analysis, an obtained sequence result was subjected to searching and similarity comparing in a GeneBank by using BLAST, and a new-found strain identified as *Lactobacillus casei* in a sequencing result is selected and preserved at −80° C. for later use.

Example 12 PFOA-Adsorbing Ability of Different Lactobacilli In Vitro

The *Lactobacillus casei* CCFM1052 and other lactobacilli as a control were purified and activated, inoculated in an MRS liquid medium at an inoculation quantity of 1% (v/v), and cultured at 37° C. for 18 h. The bacteria were collected by centrifugation at 8,000 r/min for 5 min, a precipitate was cleaned with normal saline and centrifuged at 8,000 r/min for 5 min, and the precipitate was taken to obtain live bacterial cells, that is, wet bacteria. The wet bacteria were resuspended in a 10 mg/L PFOA solution, and the final bacterial cell concentration reached 1 g Dry bacteria/L. As a blank control, wet bacteria were resuspended in ultrapure water without PFOA. A 0.1 M NaOH or HCl solution was used to quickly adjust a pH of the PFOA solution containing the bacterial solution to 3.0, where an ionic strength of a small amount of NaOH or HCl (less than 0.5 ml) has a negligible effect on PFOA adsorption. Subsequently, a 250-ml conical flask containing 100 ml of an obtained sample solution was placed in a shaker at 37° C. and 150 rpm for cultivation, a sample was taken for determination after 6 h, and an average value of 2 parallel tests was taken. The determination methods were shown in example 2 and results were shown as Table 3. The adsorption quantity of 10 mg/L PFOA by the CCFM1052 was 60%±3.2% and the adsorption quantity of the PFOA by other *Lactobacillus fermentum* was less than 45%.

TABLE 3

Adsorption rates of PFOA by different strains

| | Strains | | | | | |
|---|---|---|---|---|---|---|
| | HN11-1 | CCFM1052 | HN13-3 | NT9-8 | NT5-1 | NH18-3 |
| Adsorption rate of PFOA | 38% ± 1.5% | 60% ± 3.2% | 30% ± 2% | 41% ± 2% | 32% ± 1.8% | 28% ± 1.5% |

50 6-week-old male C57BL/6J mice were selected. After one week of adaptation to the environment, the mice were randomly divided into five groups according to body weight: a control group, a model group, a quercetin intervention group, a *Lactobacillus casei* 15-7 intervention group and an LGG intervention group with 10 mice in each group. Animal grouping and treatment methods were as shown in example 4.

Figure 12:
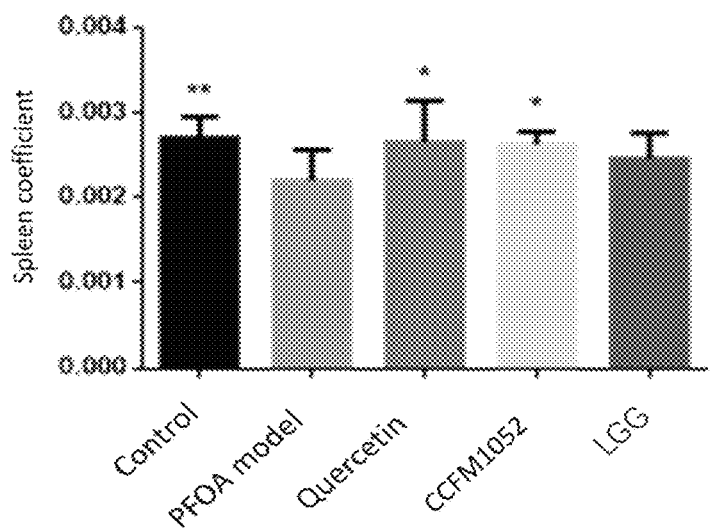
FIG. 12 is a diagram showing a change of a spleen coefficient of mice exposed to PFOA after 10 days of intervention with different substances, where *P<0.05 and **P<0.01 (vs the model group).

The results were shown in FIG. 12. The *Lactobacillus casei* CCFM1052 can significantly reverse spleen atrophy of the mice caused by PFOA exposure.

Figure 13:
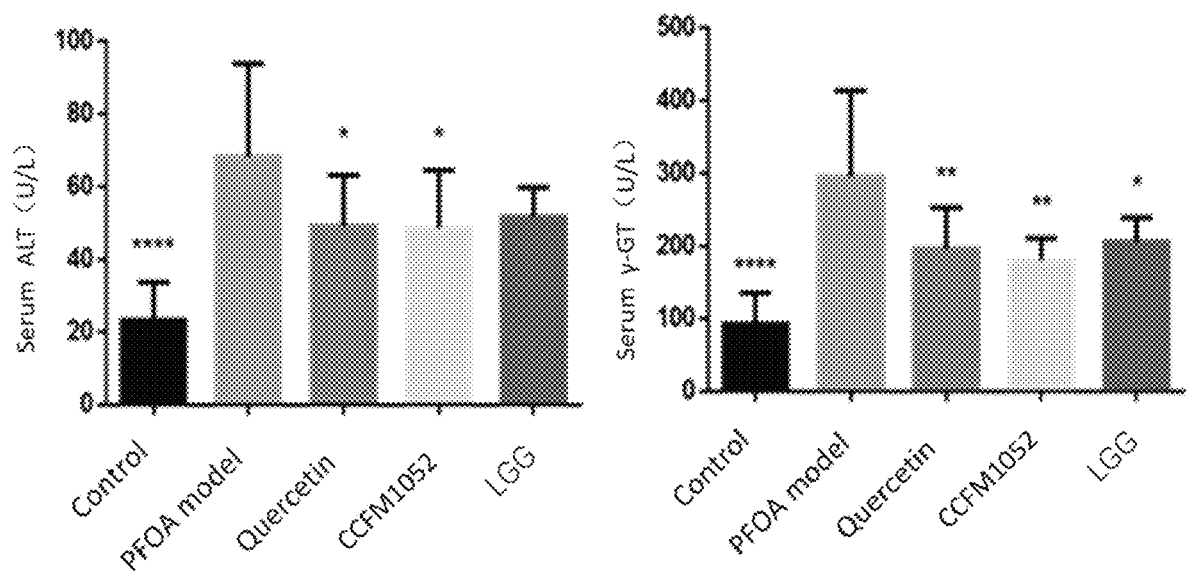
FIG. 13 is a schematic diagram levels of serum alanine transaminase (ALT) and γ-glutamyl transpeptidase (γ-GT) in the mice exposed to PFOA after 10 days of intervention with different substances, where *P<0.05, P<0.01 and **P<0.0001 (vs the model group).

Example 13 The *Lactobacillus casei* CCFM1052 can Significantly Decrease Serum Alanine Transaminase (ALT) and γ-Glutamyl Transpeptidase (γ-GT) Levels in Mice Exposed to PFOA The mice in example 12 were weighed on the $13^{th}$ day and euthanized. Blood was taken from an eye socket and centrifuged at 3,000 rpm/min for 15 min to obtain serum. Serum alanine transaminase (ALT) and α-glutamyl transpeptidase (γ-GT) levels were detected by using a fully automatic biochemical analyzer. ALT mainly existed in a soluble part of hepatocyte protoplasm and an increase of ALT activity indicated that hepatocytes were destroyed and cell membrane permeability was enhanced. The results showed in FIG. 13 that the *Lactobacillus casei* CCFM1052 can significantly decrease serum ALT and γ-GT content in the mice exposed to PFOA. The results showed that the *Lactobacillus casei* 8-9 can significantly relieve damages to a structure and a function of mouse hepatocyte membranes caused by PFOA. The ALT decreased from 68.8±15.2 U/L in the PFOA model group to 55.2±11.8 U/L and the γ-GT decreased from 310.5±80.3 U/L in the PFOA model group to 180.3±18.9 U/L.

Example 14 The *Lactobacillus casei* CCFM1052 can Significantly Decrease Activity of Superoxide Dismutase (SOD) and Content of Malondialdehyde (MDA) in a Liver Homogenate of the Mice Exposed to PFOA The mice in example 12 were weighed on the $13^{th}$ day and euthanized, and the liver was taken. A certain weight of a liver tissue was weighed on ice, pre-cooled normal saline was added at a ratio of 1:9, the tissue was homogenized to obtain a 10% liver homogenate, and the homogenate was centrifuged at 4,000×g for 15 min to obtain a supernatant. The protein concentration of the liver homogenate was determined according to the instructions. The MDA content was calculated according to the following formula: MDA content (nmol/mgprot)=[(measured OD value−control OD value)/(standard OD value−blank OD value)]× standard concentration (nmol/mL)÷protein concentration of sample to be tested (mgprot/mL)

A certain weight of a liver tissue was weighed on ice, pre-cooled normal saline was added at a ratio of 1:9, the tissue was homogenized to obtain a 10% liver homogenate, and the homogenate was centrifuged at 4,000×g for 15 min to obtain a supernatant. The protein concentration of the liver homogenate was determined according to the instructions. The SOD content was calculated according to the following formula:

SOD inhibition rate (%)=[(*A* control−*A* control blank)−(*A* test−*A* test blank)]/(*A* control−*A* control blank)

Figure 14:
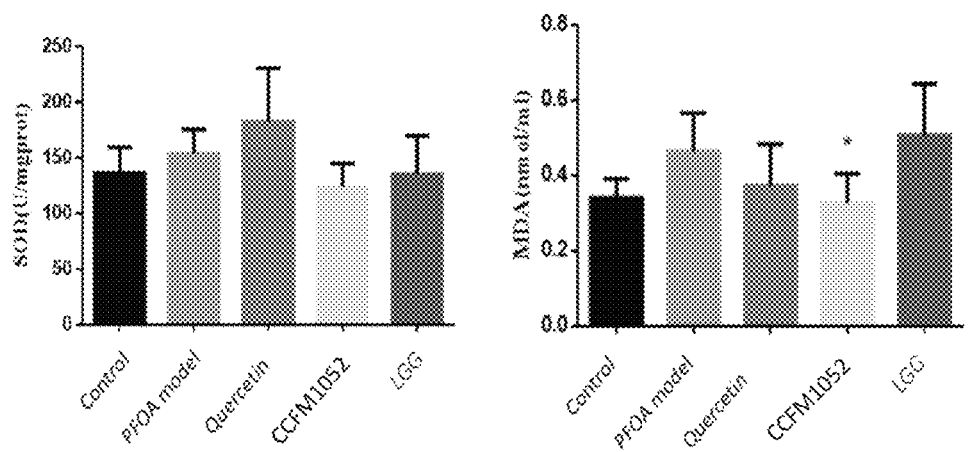
FIG. 14 shows changes of activity of superoxide dismutase (SOD) and content of malondialdehyde (MDA) in a liver homogenate of the mice exposed to PFOA after 10 days of intervention with different substances, where *P<0.05 (vs the model group).

SOD activity (U/mL)=SOD inhibition rate÷50%× dilution ratio of reaction system×dilution ratio before sample testing The results showed in FIG. 14 that the *Lactobacillus casei* CCFM1052 can significantly decrease activity of SOD and content of MDA in the liver homogenate of the mice exposed to PFOA. Under normal circumstances, generation and elimination of reactive oxygen species (ROS) in cells are effectively controlled by body and the ROS is in a state of dynamic equilibrium. If cells are unbalanced by an oxidative stress, an accumulation of the ROS can damage DNA, proteins and lipids. The SOD is an important antioxidant enzyme in the body. The MDA is a main product of lipid peroxide degradation and its content indirectly reflects severity of free radical attack on body cells. The *Lactobacillus casei* CCFM1052 can significantly reduce the free radical attack of the mice exposed to PFOA, significantly relieve an oxidative stress level in the liver tissue, and reduce liver damage in the mice exposed to PFOA.

Example 15 The *Lactobacillus casei* CCFM1052 can Significantly Decrease Abundance of *Allobaculum*, Increase Abundance of Clostridiaceae, *Adlercreutzia* and *Bacteroides* in the Intestinal Tract of the Mice Exposed to PFOA, Relieve Intestinal Disorder Caused by PFOA Exposure and Reduce Occurrence of Liver Disease and Metabolic Diseases The fresh feces of the mice on the $12^{th}$ day in example 12 was taken and the total DNA in the mouse feces sample was extracted by using an MP feces kit. The specific operation steps were as follows mainly referring to the kit instructions. Mouse feces genome was used as a template, a forward primer 520F (5'-AYTGGGYDTAAAGNG-3', SEQ ID NO. 1) and a reverse primer 802R (5'-TACNVGGGTATCTAATCC-3', SEQ ID NO. 2) were used for amplifying V3-V4 region fragments of 16S rDNA and a target fragment had a length about 247 bp. After a PCR reaction was over, all the PCR samples with observed target bands were subjected to electrophoresis again, a 2.0% agarose gel was prepared, electrophoresis was conducted at 120 V for 40 min, and after gel running, the target bands were quickly cut under UV light. The target band gel was recovered according to instructions of a QIAquick gel extraction kit. The DNA concentration of the samples was detected according to a Qubit DNA3.0 kit, a library was constructed according to a TurSeq DNA LT sample preparation kit and its instructions, and determination was conducted by an Illumina Miseq sequencer according to an MiSeq regent kit and its instructions. After the sequencing, sequences with a length<200 bp, primer sequences, and single sequences that cannot be spliced were removed, and standard splicing sequences with overlapping bases>10 bp and no mismatches were used. Sequences with a similarity greater than 97% were defined as an operational taxonomic unit (OTU) and species was determined by the Ribosomal Database Project (RDP) Naïve Bayesclassifier. The α-diversity and β-diversity of the samples were calculated to evaluate the bacterial diversity of the samples. The α-diversity was characterized by an index of chao1. The results were shown in FIG. 15 that the α-diversity of the intestinal flora of the mice in the model group was increased, indicating that PFOA exposure would be accompanied by a certain degree of intestinal disorder. The *Lactobacillus casei* CCFM1052 can significantly decrease the α-diversity of the intestinal flora and relieve intestinal disorder. Determining key roles of major intestinal microorganism compositions in various diseases is important for preventing or reversing dysbiosis to prevent or control diseases.

Figure 15:
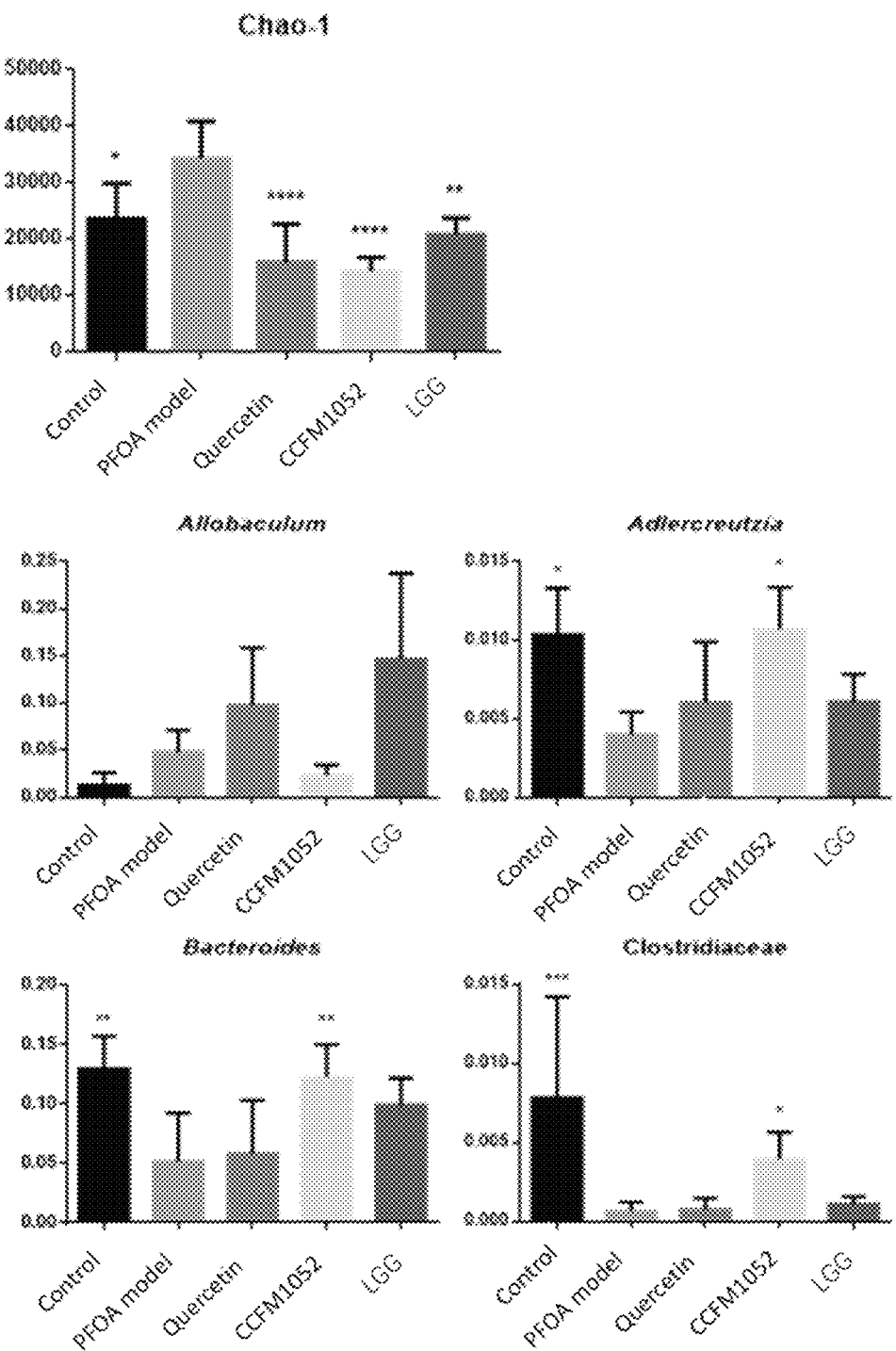
FIG. 15 is a schematic diagram of the α diversity analysis of the intestinal flora and changes of abundance of Clostridiaceae, *Adlercreutzia, Allobaculum, Bacteroides* and *Holdmania* in the intestinal tract of the mice exposed to PFOA after 10 days of intervention with different substances, where *P<0.05, P<0.01 and *P<0.001 (vs the model group).

FIG. 15 showed that the abundance of *Allobaculum* increased in the intestinal tract of the mice in the PFOA model group, while the *Lactobacillus casei* CCFM1052 could significantly reverse the situation. The abundance of *Allobaculum* also increased in the Gulf War Illness. Moreover, the increased abundance, the leaky gut and systemic endotoxemia-induced TLR4 activation further induce neuroinflammation and gastrointestinal disorder in the Gulf War Illness. Previous studies showed that the increased abundance of the *Allobaculum* may serve as one of risk indicators of hepatocellular carcinoma in females and one of key variables before onset of cancers in a host caused by carcinogen exposure. *Clostridium*, a largest group of Firmicutes, represents most diverse bacteria in human micropopulation and is a class of anaerobic, gram-positive and spore-forming rod-shaped bacteria. The *Clostridium* plays a role in regulating an immune balance in the gastrointestinal tract. Abundance of Clostridiaceae was found to be decreased in nonalcoholic fatty liver disease and obviously increased in the intestinal tract of people in a healthy control group compared with patients with chronic functional constipation. Therefore, the *Lactobacillus casei* CCFM1052 reduced the occurrence and development of non-alcoholic fatty liver disease and constipation. The *Bacteroides*, also known as Bacaeroides, belongs to Bacteroidaceae and is gram-negative, spore-free and specific anaerobic bacteria. The *Bacteroides* normally inhabits the intestines, mouth, upper respiratory tract and reproductive tract of humans and animals. The *Bacteroides* is a large number of normal flora in humans and animals, accounting for more than ¼ of the intestinal flora of an adult individual. The *Bacteroides* is a nutrient source for gut bacteria, regulates expressions of a variety of host genes, including those involved in nutrient absorption, mucosal barrier strengthening, and angiogenic factor production, activates T cell-dependent immune responses, affects expressions of Paneth cell proteins and restricts colonization of pathogens in the gastrointestinal tract. In metabolic disease clinical studies, the *Bacteroides* was an inverse relationship with obesity and related metabolic disease parameters. In an animal experiment of a high-glucose diet, the abundance of the *Bacteroides* in a high-glucose diet group was significantly lower than that in a normal group. The *Adlercreutzia* was a class of anti-inflammatory microorganisms, originally found in human feces, capable of producing short-chain fatty acids, and reduced in intestinal flora of patients with primary sclerosing cholangitis and multiple sclerosis. During a process of using traditional Chinese medicines to treat mice with type 2 diabetes, their hyperglycemia, lipid metabolism dysfunction and inflammation were significantly improved, while the abundance of the *Adlercreutzia* was significantly increased, indicating that the *Adlercreutzia* was closely associated with type 2 diabetes.

Example 16 The *Lactobacillus casei* CCFM1052 can Increase the Content of Acetic Acid and Butyric Acid in the Intestinal Tract of the Mice Exposed to PFOA Fresh feces of the mice on the $12^{th}$ day in example 12 was taken and 100 mg of the feces were weighed into a 2-mL EP tube; 500 μL of saturated NaCl was added and the feces were shaken evenly (after the feces were soaked for 30 min, the feces were ground by a tissue grinder at 70 Hz/30 s, shaken and crushed 3 times); 40 μL of 10% sulfuric acid was added, vortex shaking was conducted evenly for 30 s; 1 mL of ether was added, vortex shaking was conducted evenly, and centrifugation was conducted at 18,000×g for 15 min at 4° C.; after the centrifugation, a supernatant was taken and transferred to a new 2-mL EP tube and 0.25 g of anhydrous sodium sulfate was added; centrifugation was conducted at 18,000×g for 15 min at 4° C.; and 500 μL of the supernatant was put into a gas phase vial, and computer operating was conducted.

Figure 16:
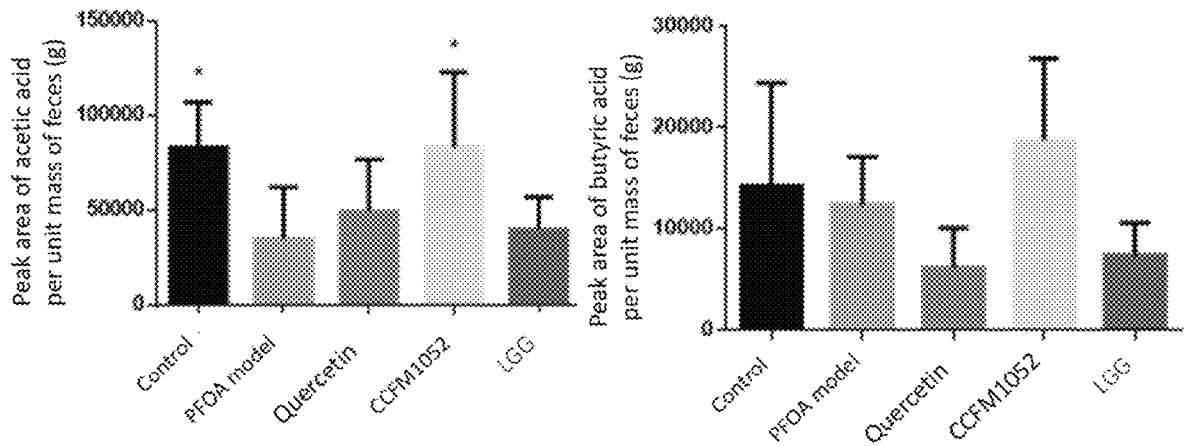
FIG. 16 shows changes of the content of acetic acid and butyric acid in the intestinal tract of the mice exposed to PFOA after 10 days of intervention with different substances, where *P<0.05 (vs the model group).

Short-chain fatty acids (SCFAs) provide energy for intestinal mucosal cells, maintain integrity of an intestinal barrier, regulate inflammatory responses, and inhibit proliferation of pathogens. Acetic acid can enable Caco-2 cells to maintain epithelial integrity during invasion by enterohemorrhage *Escherichia coli* and also increase secretion of host antimicrobial peptides to exert an antimicrobial effect. Butyric acid is a main energy source of intestinal epithelial cells, can provide energy for oxidation of the intestinal epithelial cells, maintains a water and electrolyte balance and regulates an intestinal flora balance and an intestinal barrier. Moreover, the butyric acid can inhibit tumor cell proliferation and differentiation and induce apoptosis at a millimolar concentration, and activate an expression of a sodium/glucose cotransporter gene (SLC5A8) to induce apoptosis. In addition, oral butyrate is beneficial for progression of diabetes. The short-chain fatty acids can exert an anti-inflammatory effect through an activation pathway of G protein-coupled receptors (GPCRs) and an inhibitory pathway of histone deacetylases (HDACs), and have a significant relieving effect on inflammatory bowel disease (IBD). FIG. 16 showed determination of the short-chain fatty acids in feces. The *Lactobacillus casei* CCFM1052 can significantly increase the content of the acetic acid in the intestinal tract of mice exposed to PFOA (P<0.05), restore the content of the acetic acid to a normal level, improve the content of the butyric acid and helps maintain a microbial balance in the intestinal tract.

Example 17 The *Lactobacillus casei* CCFM1052 can Relieve Constipation of Mice

40 SPF male BALB/c mice (20-25 g) were randomly divided into 5 groups: a blank control group, a constipation model control group, a *Lactobacillus casei* CCFM1052 intervention group, a *Lactobacillus plantarum* control group and a phenolphthalein treatment control group with 10 mice in each group.

The freeze-dried *Lactobacillus casei* CCFM1052 powder was resuspended in skim milk powder to prepare a bacterial suspension with a concentration of $4.0 \times 10^9$ CFU/mL. 14 days before an experiment, the mice in the intervention group were gavaged with 0.25 mL of the *Lactobacillus casei* CCFM1052 skim milk suspension with a concentration of $4.0 \times 10^9$ CFU/mL every day, the mice in the *Lactobacillus plantarum* control group were gavaged with an equal amount of *L. plantarum* ST-III and the mice in the other 3 groups were gavaged with an equal amount of bacteria-free skim milk. On the $15^{th}$ to $17^{th}$ day of the experiment, the mice in the negative control group were gavaged with 0.25 mL of normal saline and the mice in the other four groups were gavaged with 0.25 mL of a loperamide solution at 1 mg/mL to ensure that the gavage amount of loperamide in the mice was 10 mg/kgBW.

One hour after the gavage, the mice in the negative control group and the constipation model control group were gavaged with skim milk, the mice in the *Lactobacillus casei* CCFM1052 intervention group was gavaged with 0.25 mL of *Lactobacillus casei* CCFM1052 at a concentration of $4.0 \times 10^9$ CFU/mL, and the mice in the phenolphthalein treatment control group was gavaged with 0.25 mL of a phenolphthalein solution at 7 mg/mL to ensure that the gavage amount of phenolphthalein in the mice was 70 mg/kgBW. The mice in the *Lactobacillus plantarum* group was gavaged with 0.25 mL of *L. plantarum* ST-III at $4.0 \times 10^9$ CFU/mL.

The mouse feces were collected every day during the experiment period for determining the fecal water content of the mice. The fecal water content was calculated by using the following formula. Fecal water content (%)=(wet weight of feces−dry weight of feces)/wet weight of feces×100. On the morning of the $17^{th}$ day, the mice in the blank control group were gavaged with normal saline, the mice in the other groups were gavaged with loperamide, after the gavage for 1 h, all the mice were gavaged with 0.25 mL of an activated carbon arabic gum aqueous solution, each mouse was separately placed in a clean stainless steel cage covered with absorbent paper, time (min) from start of the gavage with the activated carbon to defecation of first black stool was recorded as first black stool defecation time to evaluate an effect of the *Lactobacillus casei* CCFM1052 on constipation of the mice, and during the period, the mice ate and drank freely.

Figure 17:
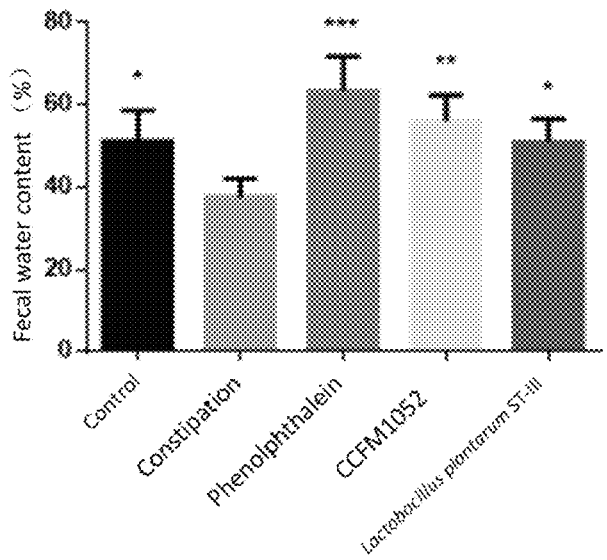
FIG. 17 shows improvement of fecal water content in mice with constipation after intervention with the strain of the present disclosure, where *P<0.05, P<0.01 and *P<0.001 (vs the model group).
Figure 18:
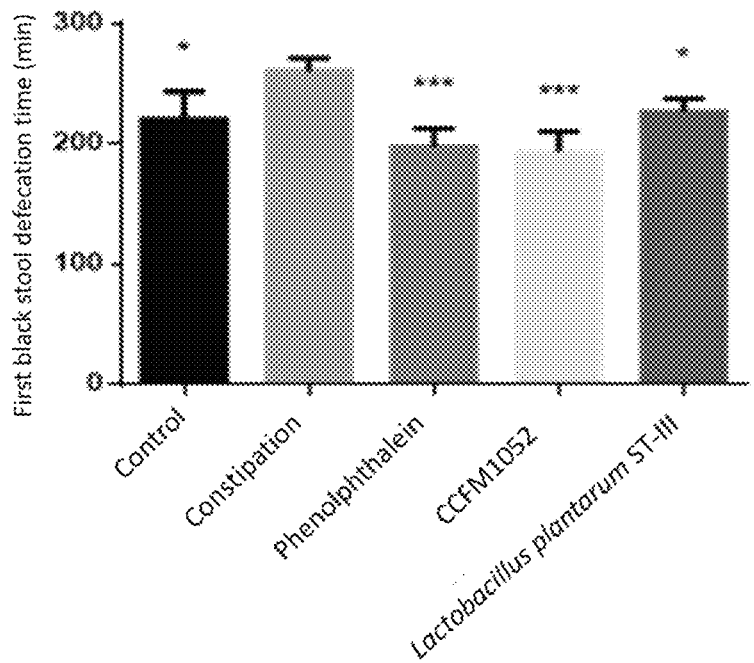
FIG. 18 shows decrease of first black stool defecation time in the mice with constipation after intervention with the strain of the present disclosure, where *P<0.05 and ***P<0.001 (vs the model group).

FIG. 17 showed determination results of the fecal water content of the mice that the fecal water content was significantly decreased in the constipation model group, while the fecal water content of the mice with constipation was extremely significantly increased in the phenolphthalein treatment group ($P<0.001$), and the *Lactobacillus casei* CCFM1052 had a better relieving effect on the fecal water content of the mice with constipation ($P<0.01$) than that of the control strain *Lactobacillus plantarum* ST-III ($P<0.05$). The results of first black stool in mice showed in FIG. 18 that the first black stool defecation time of the mice was significantly delayed in the constipation model group, while the defecation time of the mice with constipation was significantly shortened in the phenolphthalein treatment group ($P<0.001$), the *Lactobacillus casei* CCFM1052 had an excellent effect of shortening the first black stool defecation time as the phenolphthalein ($P<0.001$), and the *Lactobacillus plantarum* ST-III also significantly shortened the first black stool defecation time ($P<0.05$), but had the effect obviously not as good as that of the *Lactobacillus casei* CCFM1052.

Example 18 The *Lactobacillus casei* CCFM1052 Promote Proliferation and MafA mRNA Expression of High Glucose-Induced INS-1 Cells In an experiment, 5 groups were divided: a normal group (a normal culture solution containing 11.1 mmol/L of glucose), a high glucose group (a high glucose culture solution containing 22.2 mmol/L of glucose), a rosiglitazone group (a high glucose culture solution+80 µmol/L of rosiglitazone), a CCFM1052 group (a high glucose culture solution+$1 \times 10^9$ CFU/mL of a CCFM1052 bacterial solution) and an LGG group (a high glucose culture solution+$1 \times 10^9$ CFU/mL of a LGG bacterial solution).

INS-1 cells (code: BH-AC0530) were cultured in a RPMI-1640 culture solution (containing 11.1 mmol/L of glucose, 10% of FBS, 50 µmol/L of 2-mercaptoethanol, 1 mmol/L of pyruvic acid and 10 mmol/L of HEPES) and placed in a 5% $CO_2$ incubator at 37° C.

Determination of cell proliferation by a CCK-8 assay: the cells in a good state were digested and centrifuged, the treated cells were inoculated on a 96-well plate with about $5 \times 10^3$ cells in each well, no cells were inoculated into peripheral wells of the plate to prevent an edge effect, and a PBS solution was added at the same time. After the cells adhered to walls, a RPMI-1640 medium containing 0.5% fetal bovine serum was added to each well, and a synchronized treatment was conducted for 24 h. At the end of the synchronization, corresponding medium was added into each well according to the grouping, culture was conducted for 48 h, three duplicate wells were arranged in each group and a zero-adjustment well was arranged. After drug intervention, an old medium was aspirated, the cells were washed twice with PBS, 180 µL of a serum-free medium and 20 µL of a CCK-8 solution were added, and the cells were incubated for 3-4 h. After the incubation, the absorbance of each well was measured at 450 nm by using a microplate reader.

Determination of MafA mRNA expression: RNA was extracted by a Trizol method, an original culture solution in a 6-well plate was discarded, the cells were washed twice with pre-cooled PBS, the cells were lysed by adding 1.0 mL of Trizol in each well, a lysate containing the cells was transferred to an enzyme-free EP tube, the lysate was pipetted until there was no obvious precipitate and standing was conducted for 5 min. 0.2 mL of chloroform was added to each EP tube, vigorous shaking was conducted for 15 s, and an obtained solution was placed at a room temperature for 2-3 min. The obtained solution was centrifuged at 12,000 rpm for 15 min at 4° C., about 0.4 mL of a supernatant was aspirated and transferred to another enzyme-free EP tube, 0.5 mL of isopropanol was added, an obtained mixture was inverted and mixed uniformly, and standing was conducted at a room temperature for 10 min. The standing solution was centrifuged at 12,000 rpm for 10 min at 4° C., a supernatant was discarded carefully, 1.0 mL of 75% ethanol was added and an obtained mixture was inverted and mixed uniformly. The obtained mixture was centrifuged at 12,000 rpm for 5 min at 4° C., a supernatant was discarded, and drying was conducted at a room temperature for 2-5 min. 20 µL of DEPC-treated water was added for dissolving and an obtained product was stored at 80° C. for standby use. The concentration and mass of RNA were determined and a reverse transcription was conducted according to the instructions of a reverse transcription kit. A cDNA obtained by the reverse transcription was detected by qRT-PCR, where MafA specific primers were as follows: F: 5'-atcactctgcc-caccatcac-3' (SEQ ID NO. 3) and R: 5'-atgacctcctccttgctgaa-3' (SEQ ID NO. 4). PCR system: F (10 μM), 0.50 μL; R (10 μM), 0.50 μL; c. DNA template, 1.00 μL; dd $H_2O$, 3.00 μL; and mix, 5.00 μL. PCR program was as follows: 95° C., 2 min;

(95° C., 30 sec; 60° C., 30 sec; 72° C., 20 sec)*35; and 72° C., 5 min; and after the target gene was detected by real-time PCR, the relative gene expression was analyzed by a $2^{-\Delta\Delta CT}$ method. An expression level of a target gene in the INS-1 cells of each group of rats was analyzed by using a CFX Manager software, the expression level of the normal group was taken as 1, and compared with the normal group, the gene expression levels of other groups were calculated.

Figure 19:
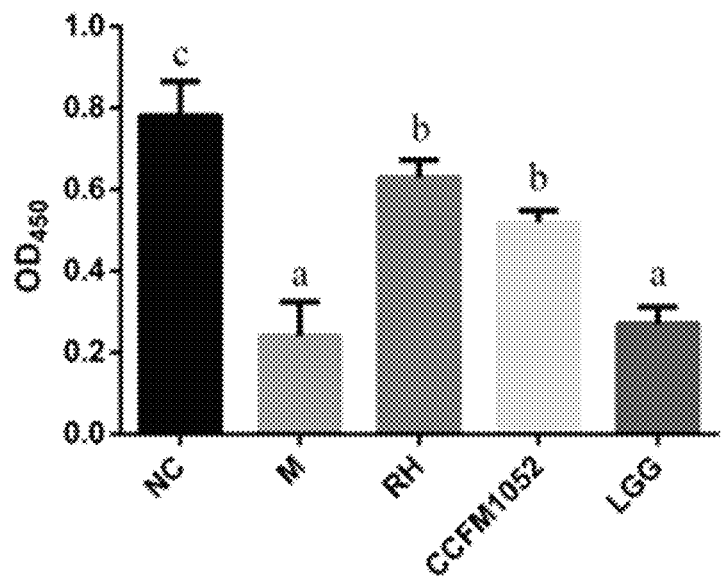
FIG. 19 shows effects of the strain of the present disclosure on proliferation of INS-1 cells under high glucose.

The results of the CCK-8 assay were shown in FIG. 19. Compared with the normal group, the cell growth in the high glucose group was significantly decreased ($P<0.05$); the cell proliferation in the rosiglitazone control group was significantly increased compared with that in the high glucose group ($P<0.05$); and the cell proliferation in the CCFM1052 group was also significantly increased compared with that in the high glucose group ($P<0.05$).

Figure 20:
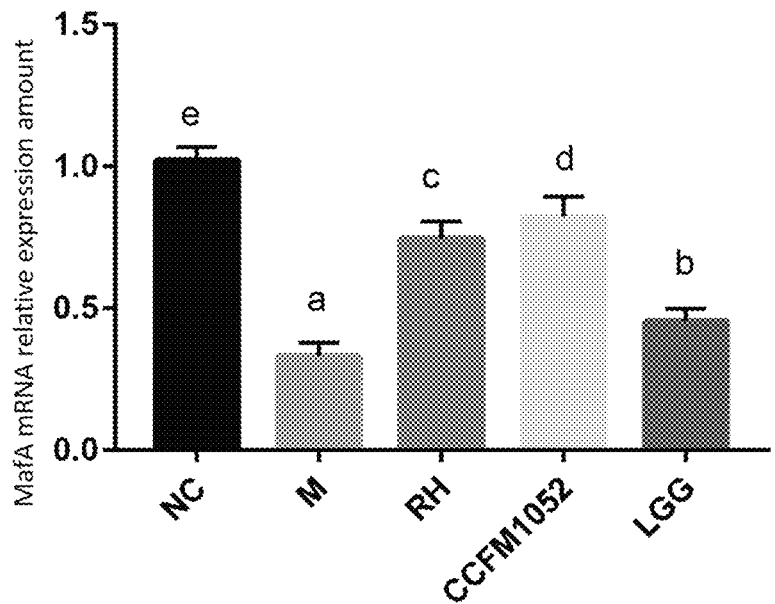
FIG. 20 shows effects of the strain of the present disclosure on MafA gene expression of INS-1 cells under high glucose.

The expression of MafA mRNA was shown in FIG. 20. The expression of the MafA mRNA in the high glucose group was significantly lower than that in the normal group ($P<0.05$), while the expression of the MafA mRNA in the rosiglitazone positive control group and CCFM1052 group was significantly increased compared with that in the high glucose group (both $P<0.05$).

Example 19 Preparation of Fermented Food Containing the Bacteria Using the *Lactobacillus casei* CCFM1052 of the Disclosure (1) Preparation of Fruit and Vegetable Drink Fresh vegetables were selected, thoroughly cleaned, and juiced, and then high-temperature instant sterilization was performed. After high-temperature heat sterilization at 140° C. for 2 s, the temperature was immediately lowered to 37° C. Then the *Lactobacillus casei* CCFM1052 prepared in the disclosure was inoculated to make the concentration reach above $10^6$ CFU/ml. The juice product was stored under refrigeration at 4° C., and thus, the fruit and vegetable beverage containing live bacteria of the *Lactobacillus casei* CCFM1052 of the disclosure was obtained. The fruit and vegetable product included cucumber, carrot, beet, celery and cabbage products.

(2) Preparation of Fermented Dairy Product

The *Lactobacillus casei* CCFM1052 was inoculated into raw materials of a dairy product or a bean product to prepare a fermented dairy product or a fermented bean product; the fermented food included the fermented dairy product or the fermented bean product; and the dairy product included milk, sour cream and cheese.

(3) The *Lactobacillus casei* CCFM1052 was inoculated into solid, semi-solid or liquid raw materials for fermentation to prepare a solid fermented food, a liquid fermented food and a semi-solid fermented food.

Similar to a use effect of the *Lactobacillus casei* CCFM1052, the *Lactobacillus casei* CCFM1052 can significantly relieve liver toxicity and intestinal flora imbalance caused by PFOA exposure and can significantly relieve constipation by *Lactobacillus casei* CCFM1052 and use thereof. The fermented food containing the *Lactobacillus casei* CCFM1052 has a high adsorption effect on PFOA in vitro, is not colonized in the intestinal tract, significantly relieves liver oxidative stress injury and serum biochemical indicators caused by PFOA, significantly relieves spleen atrophy caused by the PFOA exposure, significantly relieves dysregulation of intestinal microorganisms of Clostridiaceae, *Adlercreutzia*, *Allobaculum* and *Bacteroides* caused by the PFOA exposure, significantly relieves a metabolic disorder of intestinal flora caused by PFOA exposure, significantly increases the content of acetic acid and propionic acid in the intestinal tract, significantly improves fecal water content and decreases first black stool defecation time of mice with constipation. In addition, the fermented food containing the *Lactobacillus casei* CCFM1052 and can significantly improve proliferation and MafA gene expression of INS-1 cells under high glucose and relieve PFOA-related diabetes.

The *Lactobacillus casei* CCFM1052 of the present disclosure can be used for preparing a medicine combination and the fermented food for relieving PFOA toxicity and constipation, reduces occurrence of liver diseases, metabolic diseases and potential carcinogenicity, and has broad use prospects.

Example 20 Screening and Identification of *Lactobacillus buchneri* CCFM1053

(I) Separating and Screening of Lactobacilli:

(1) 100 μL of pickled vegetable water was taken. The taken sample was enriched in an MRS medium containing sorbitol at 35° C. for 12 h;

(2) performing gradient dilution of the enriched samples, spreading the samples subjected to gradient dilution on MRS solid plates supplemented with 0.02% bromcresol purple, and performing culturing for 24-48 h;

(3) selecting single colonies with obvious color-changing zones and conforming to the basic morphology of lactobacilli, performing plate streaking purification, and screening and isolating lactobacilli;

(4) culturing the above single colonies in liquid MRS culture solutions for 24 h, then performing Gram staining, and selecting Gram-positive bacteria for performing subsequent experiments.

(II) Preliminary Identification of Lactobacilli: Calcium-Dissolving Zone Determination Method:

(1) culturing the lactobacilli screened in step (I) in a liquid sorbitol MRS culture solution for culturing the lactobacilli for 24 h, then taking 1 mL of the culture and centrifuging the culture at 8000 rpm for 2 min;

(2) the centrifuged culture was washed twice with a 0.05 M $KH_2PO_4$ solution;

(3) resuspending the obtained bacterial sludge, streaking the bacterial sludge on a sorbitol MRS-0.75% $CaCo_3$ solid medium, and culturing for 24 h;

(4) selecting colonies with obvious calcium-dissolving zones and being convex-round, fine and white without mycelia, and after Gram staining, preliminarily judging the bacteria as *Lactobacillus* if the bacterial cells were bacilliform as observed under microscope.

(III) Molecular Biological Identification of *Lactobacillus Buchneri*:

(1) a genome of single bacteria was extracted:

A. the lactobacilli screened out in step (II) were cultured overnight, 1 mL of a bacterial suspension cultured overnight was put into a 1.5 mL centrifuge tube and centrifuged for 2 min at 10,000 rpm, and bacteria were obtained after supernatant was discarded;

B. the bacteria were purged with 1 mL of sterile water and then centrifuged for 2 min at 10,000 rpm, and bacteria were obtained after supernatant was discarded;

C. 200 μL of SDS lysate was added for water bath for 30 min at 80° C.;

D. 200 μL of a phenol-chloroform solution was added to bacteria lysate, after bottom-up even mixing, centrifugation was performed for 5-10 min at 12,000 rpm, and 200 μL of supernatant was taken, where the phenol-chloroform solution had compositions of Tris-saturated phenol, chloroform and isoamyl alcohol according to a volume ratio of 25:24:1;

E. 400 μL of ice alcohol or ice isopropyl alcohol was added to 200 μL of supernatant to stand for 1 h at −20° C. and was then centrifuged for 5-10 min at 12,000 rpm, and supernatant was discarded;

F. 500 μL of 70% (volume percentage) ice alcohol was added for resuspending and precipitating and centrifuged for 1-3 min at 12,000 rpm, and supernatant was discarded;

G. drying was performed with an oven at 60° C., or air-drying was performed; and H. 50 μL of ddH$_2$O was added for redissolving and precipitating for PCR; and (2) performing 16S rDNA PCR:

A. 50 μL PCR reaction system of 16S rDNA of bacteria: 10×Taq buffer, 5 μL; dNTP, 5 μL; 27F, 0.5 μL; 1492R, 0.5 μL; Taq enzyme, 0.5 μL; template, 0.5 μL; ddH$_2$O, 38 μL.

B. PCR conditions:

95° C., 5 min; 95° C., 10 s; 55° C., 30 s; 72° C., 30 s; steps 2-4, 30×; 72° C., 5 min; 12° C., 2 min;

(3) preparing a 1% agarose gel, then mixing the PCR product with 10× loading buffer, performing loading at a loading amount of 5 μL, performing running at 120 V for 30 min, and then performing gel imaging;

(4) a PCR product of 16S rDNA was subjected to sequencing analysis, an obtained sequence result was subjected to searching and similarity comparing in a GeneBank by using BLAST, and a new-found strain identified as *Lactobacillus buchneri* in a sequencing result is selected and preserved at −80° C. for later use.

Example 21 The *Lactobacillus buchneri* CCFM1053 has a Good PFOA Adsorption Capacity The *Lactobacillus buchneri* CCFM1053 and other lactobacilli as a control were purified and activated, inoculated in an MRS liquid medium at an inoculation quantity of 1% (v/v), and cultured at 37° C. for 18 h. The bacteria were collected by centrifugation at 8,000 r/min for 5 min, a precipitate was cleaned with normal saline and centrifuged at 8,000 r/min for 5 min, and the precipitate was taken to obtain live bacterial cells, that is, wet bacteria. The wet bacteria were resuspended in a 10 mg/L PFOA solution, and the final bacteria concentration reached 1 g Dry bacteria/L. As a blank control, wet bacteria were resuspended in ultrapure water without PFOA. A 0.1 M NaOH or HCl solution was used to quickly adjust a pH of the PFOA solution containing the bacterial solution to 3.0, where an ionic strength of a small amount of NaOH or HCl (less than 0.5 ml) had a negligible effect on PFOA adsorption. Subsequently, a 250-ml conical flask containing 100 ml of an obtained sample solution was placed in a shaker at 37° C. and 150 rpm for cultivation, a sample was taken for determination after 6 h, and an average value of 2 parallel tests was taken.

Figure 21:
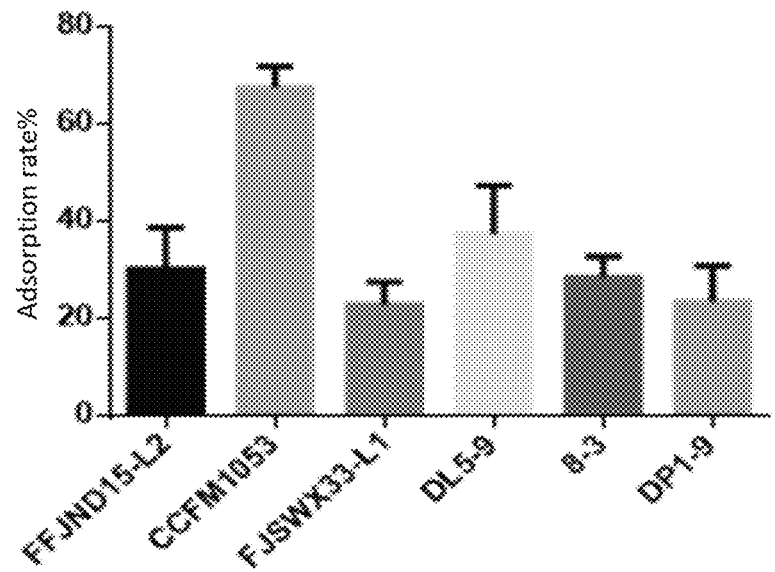
FIG. 21 is a schematic diagram of a concentration change of PFOA before and after adsorption, where after different strains were resuspended in vitro in a PFOA solution at a concentration of 10 mg/L and cultured at 37° C. in a shaker at 150 rpm for 6 h, an obtained sample solution passes through a 0.22 μm water filter membrane and enters an ultra-high performance liquid chromatography-mass spectrometer.

The determination was conducted according to the method disclosed in example 2. The adsorption quantity of PFOA by lactobacilli was calculated according to difference of the PFOA concentration before and after adsorption. The determination results were shown in FIG. 21. The adsorption rate of 10 mg/L PFOA by the CCFM1053 was 67.5%±1.2% and the adsorption rate of the PFOA by other lactobacilli was less than 40%.

Example 22 The *Lactobacillus buchneri* CCFM1053 Significantly Relieve Spleen Atrophy in Mice Exposed to PFOA 50 6-week-old male C57BL/6J mice were selected. After one week of adaptation to the environment, the mice were randomly divided into four groups according to body weight: a control group, a model group, a fluoxetine intervention group, and a *Lactobacillus buchneri* CCFM1053 intervention group, each containing 10 mice. Animal grouping and treatment methods are shown in Table 4.

Figure 22:
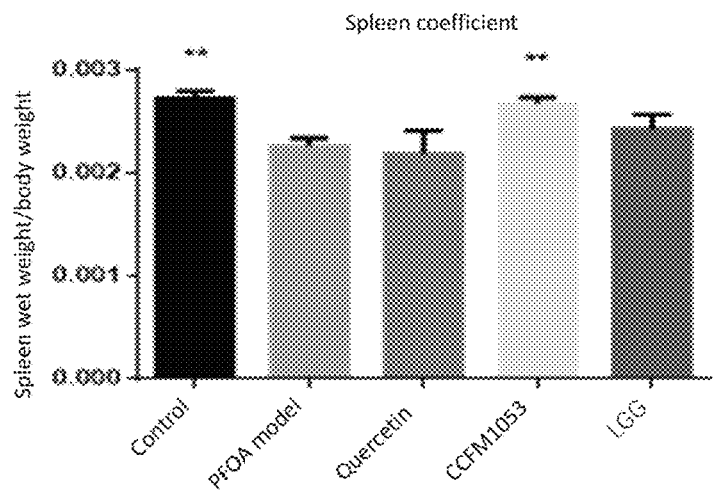
FIG. 22 is a diagram showing a change of a spleen ratio mice exposed to PFOA after 10 days of intervention with different substances, where *P<0.05 (vs the model group).

The results were shown in FIG. 22 that the *Lactobacillus buchneri* CCFM1053 can significantly reverse spleen atrophy of the mice caused by PFOA exposure.

Figure 23:
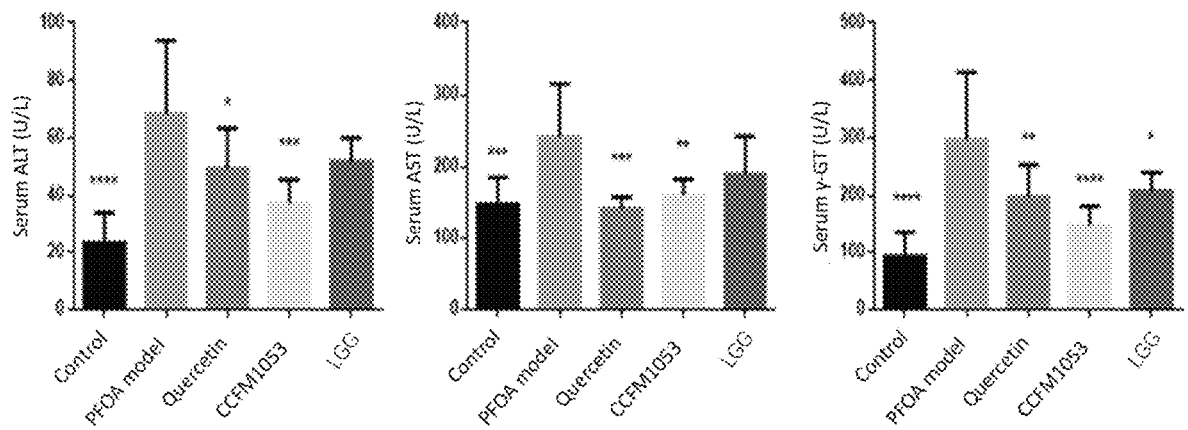
FIG. 23 is a schematic diagram of levels of serum ALT, AST and γ-GT in the mice exposed to PFOA after 10 days of intervention with different substances, where *P<0.05, P<0.01, *P<0.001 and ****P<0.0001 (vs the model group).

Example 23 The *Lactobacillus buchneri* CCFM1053 Significantly Decrease Serum ALT, AST and γ-GT in the Mice Exposed to PFOA The serum in example 22 was taken and serum ALT, AST and γ-GT content were detected by using a fully automatic biochemical analyzer. ALT mainly existed in a soluble part of hepatocyte protoplasm and an increase of ALT activity indicated that hepatocytes were destroyed and cell membrane permeability was enhanced. AST mainly existed in mitochondria of hepatocytes and an increase of AST activity indicated a mitochondrial damage. The results showed in FIG. 23 that *Lactobacillus buchneri* CCFM1053 can significantly decrease serum ALT, AST and γ-GT content in the mice exposed to PFOA. The results showed that the *Lactobacillus buchneri* CCFM1053 can significantly relieve damages to a structure and a function of mouse hepatocyte membranes caused by PFOA. The ALT decreased from 68.8±15.2 U/L in the PFOA model group to 38.3±8.9 U/L, the AST decreased from 240.7±48.2 U/L in the PFOA model group to 170.5±9.8 U/L and the γ-GT decreased from 310.5±80.3 U/L in the PFOA model group to 160.3±20.4 U/L.

Figure 24:
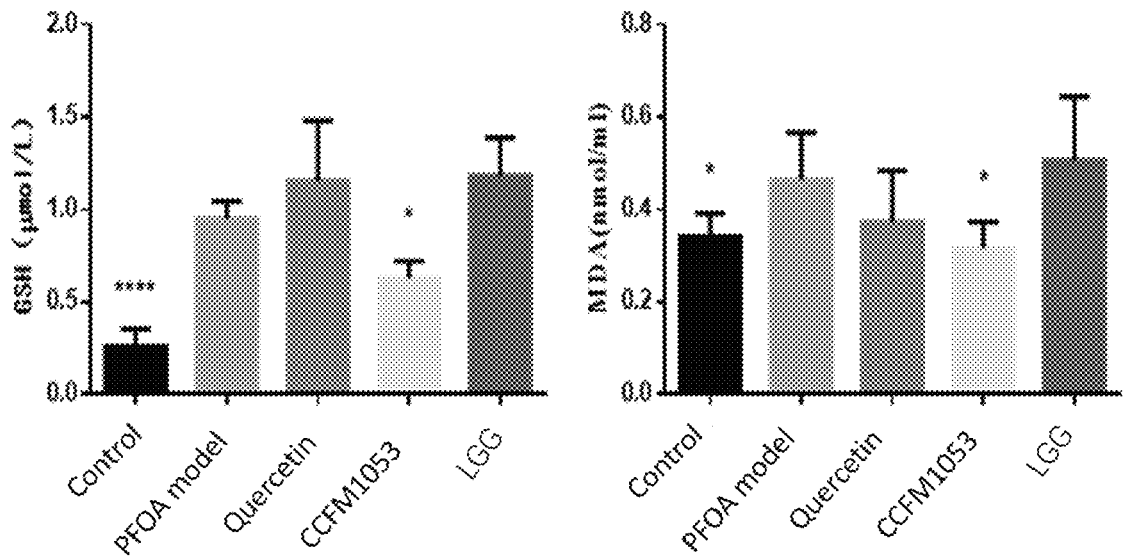
FIG. 24 is a schematic diagram of changes of GSH activity and MDA content in liver of the mice exposed to PFOA after 10 days of intervention with different substances.

Example 24 The *Lactobacillus buchneri* CCFM1053 can Significantly Decrease MDA and GSH Levels in Liver of the Mice Exposed to PFOA The mouse liver in example 22 was taken to prepare a 10% homogenate and the MDA and GSH levels in the liver were detected by using a kit purchased from Nanjing Jiancheng Research Institute. The GSH is an important antioxidant enzyme in body and has an important scavenging effect on ROS. The MDA is an end product of ROS during lipid peroxidation and can directly reflect a level of the lipid peroxidation. The results showed in FIG. 24 that the *Lactobacillus buchneri* CCFM1053 can significantly decrease the MDA and GSH content in the liver of the mice exposed to PFOA. The results indicated that the *Lactobacillus buchneri* CCFM1053 could effectively relieve liver oxidative stress injury caused by PFOA.

Figure 25:
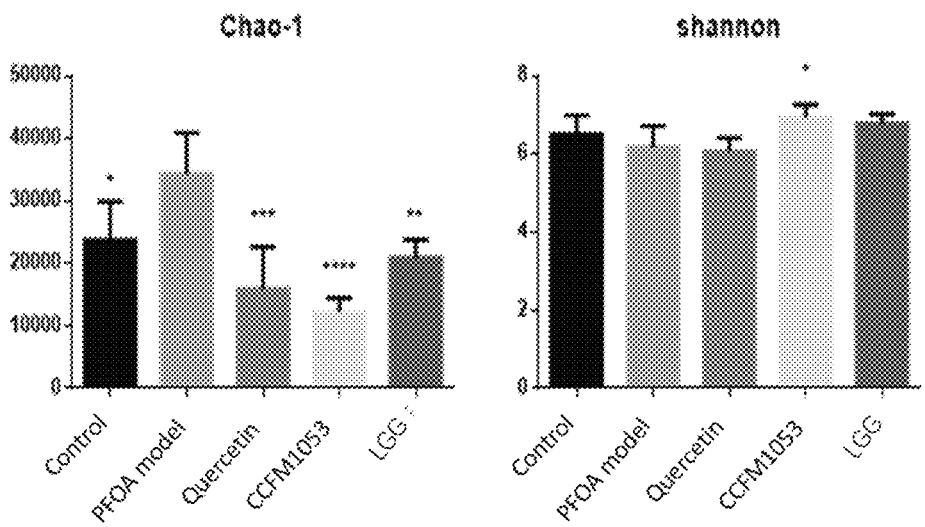
FIG. 25 is a schematic diagram of changes of the α diversity of the intestinal flora of the mice exposed to PFOA after 10 days of intervention with different substances, where *P<0.05, P<0.01 and *P<0.001 (vs the model group).

Example 25 The *Lactobacillus buchneri* CCFM1053 can Significantly Decrease Abundance of *Allobaculum* and Increase Abundance of *Bacteroides* and Eubacteriaceae in the Intestinal Tract of the Mice Exposed to PFOA, Relieve Intestinal Disorder Caused by PFOA Exposure, and Reduce Occurrence of Liver Disease The fresh feces of the mice on the 12$^{th}$ day in example 22 was taken and the total DNA in the mouse feces sample was extracted by using an MP feces kit. The specific operation steps were as follows mainly referring to the kit instructions. Mouse feces genome was used as a template, a forward primer 520F (5'-AYTGGGYDTAAAGNG-3', SEQ ID NO. 1) and a reverse primer 802R (5'-TACNVGGGTATCTAATCC-3', SEQ ID NO. 2) were used for amplifying V3-V4 region fragments of 16S rDNA and a target fragment had a length about 247 bp. After a PCR reaction was over, all the PCR samples with observed target bands were subjected to electrophoresis again, a 2.0% agarose gel was prepared, electrophoresis was conducted at 120 V for 40 min, and after gel running, the target bands were quickly cut under UV light. The target band gel was recovered according to instructions of a QIAquick gel extraction kit. The DNA concentration of the samples was detected according to a Qubit DNA3.0 kit, a library was constructed according to a TurSeq DNA LT sample preparation kit and its instructions, and determination was conducted by an Illumina Miseq sequencer according to an MiSeq regent kit and its instructions. After the sequencing, sequences with a length <200 bp, primer sequences, and single sequences that cannot be spliced were removed, and standard splicing sequences with overlapping bases>10 bp and no mismatches were used. Sequences with a similarity greater than 97% were defined as an operational taxonomic unit (OTU) and species was determined by the Ribosomal Database Project (RDP) Naïve Bayesclassifier. The α-diversity and β-diversity of the samples were calculated to evaluate the bacterial diversity of the samples. The α-diversity was characterized by indexes of chao1 and shannon. The results were shown in FIG. 25 that the α-diversity of the intestinal flora of the mice in the model group was increased, indicating that PFOA exposure would be accompanied by a certain degree of intestinal disorder. The *Lactobacillus buchneri* CCFM1053 can significantly decrease the α-diversity of the intestinal flora and relieve intestinal disorder.

Figure 26:
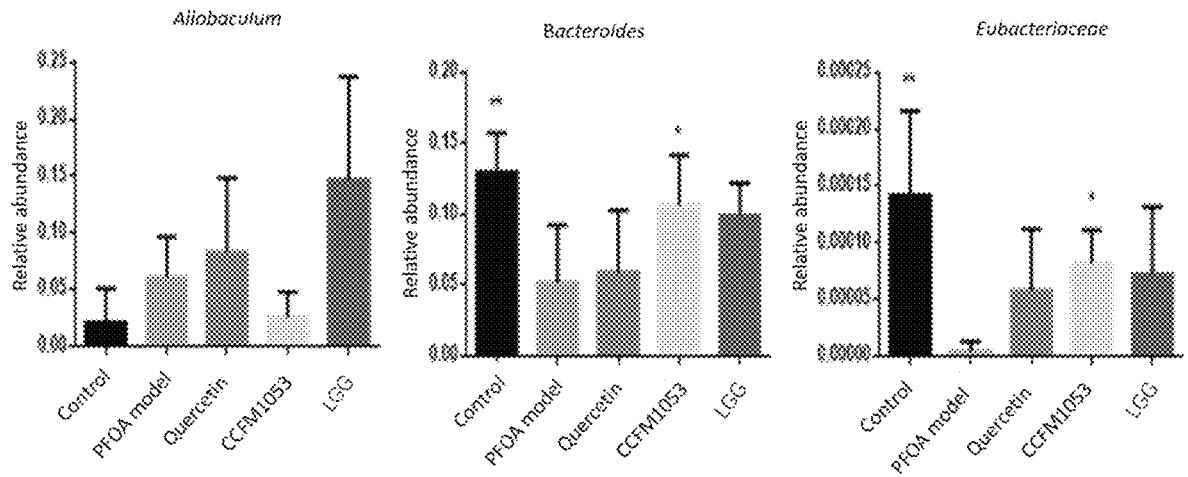
FIG. 26 is a schematic diagram of changes of abundance of Eubacteriaceae, *Bacteroides* and *Allobaculum* in the intestinal tract of the mice exposed to PFOA after 10 days of intervention with different substances, where *P<0.05 and **P<0.01 (vs the model group).

In addition, the results in FIG. 26 showed that the *Lactobacillus buchneri* CCFM1053 can also significantly increase the abundance of *Bacteroides* and Eubacteriaceae in the mice exposed to PFOA. The *Bacteroides*, also known as Bacaeroides, belongs to Bacteroidaceae and is gram-negative, spore-free and specific anaerobic bacteria. The *Bacteroides* normally inhabits the intestines, mouth, upper respiratory tract and reproductive tract of humans and animals. The *Bacteroides* is a large number of normal flora in humans and animals, accounting for more than ¼ of the intestinal flora of an adult individual. The *Bacteroides* is a nutrient source for gut bacteria, regulates expressions of a variety of host genes, including those involved in nutrient absorption, mucosal barrier strengthening, and angiogenic factor production, activates T cell-dependent immune responses, affects expressions of Paneth cell proteins and restricts colonization of pathogens in the gastrointestinal tract. The Eubacteriaceae is associated with hepatic encephalopathy, that is restoration of a dysfunctional gut-liver-brain axis in cirrhosis, and abundance of the Eubacteriaceae is significantly reduced after biliary-gut bypass in a severely obese patient. The *Lactobacillus buchneri* CCFM1053 can significantly decrease the abundance of the *Allobaculum* in the intestinal tract of the mice exposed to PFOA. The increased abundance of the *Allobaculum* may serve as one of risk indicators of hepatocellular carcinoma in females and one of the key variables before onset of cancers in a host caused by carcinogen exposure. The above results indicated that the *Lactobacillus buchneri* CCFM1053 relieved toxicity of PFOA and was also capable of regulating intestinal flora, immunity and intestinal barrier, and reducing occurrence of liver disease.

Example 26 The *Lactobacillus buchneri* CCFM1053 can Relieve Constipation of Mice 40 SPF male BALB/c mice (20-25 g) were randomly divided into 5 groups: a blank control group, a constipation model control group, a *Lactobacillus buchneri* CCFM1053 intervention group, a *Lactobacillus plantarum* control group and a phenolphthalein treatment control group with 10 mice in each group.

The freeze-dried *Lactobacillus buchneri* CCFM1053 powder was resuspended in skim milk powder to prepare a bacterial suspension with a concentration of 4.0×10$^9$ CFU/mL. 14 days before an experiment, the mice in the intervention group were gavaged with 0.25 mL of the *Lactobacillus buchneri* CCFM1053 skim milk suspension with a concentration of 4.0×10$^9$ CFU/mL every day, the mice in the *Lactobacillus plantarum* control group were gavaged with an equal amount of *L. plantarum* ST-III and the mice in the other 3 groups were gavaged with an equal amount of bacteria-free skim milk. On the 15$^{th}$ to 17$^{th}$ day of the experiment, the mice in the negative control group were gavaged with 0.25 mL of normal saline and the mice in the other four groups were gavaged with 0.25 mL of a loperamide solution at 1 mg/mL to ensure that the gavage amount of loperamide in the mice was 10 mg/kgBW.

One hour after the gavage, the mice in the negative control group and the constipation model control group were gavaged with skim milk, the mice in the *Lactobacillus buchneri* CCFM1053 intervention group was gavaged with 0.25 mL of *Lactobacillus buchneri* CCFM1053 at a concentration of 4.0×10$^9$ CFU/mL, and the mice in the phenolphthalein treatment control group was gavaged with 0.25 mL of a phenolphthalein solution at 7 mg/mL to ensure that the gavage amount of phenolphthalein in the mice was 70 mg/kgBW. The mice in the *Lactobacillus plantarum* group was gavaged with 0.25 mL of *L. plantarum* ST-III at 4.0×10$^9$ CFU/mL.

The mouse feces were collected every day during the experiment period for determining the fecal water content of the mice. The fecal water content was calculated by using the following formula.

Fecal water content (%)=(wet weight of feces−dry weight of feces)/wet weight of feces×100.

Figure 27:
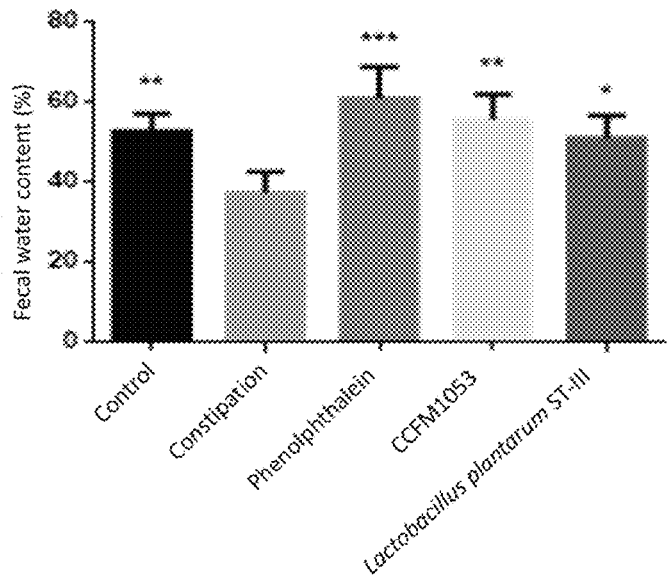
FIG. 27 shows improvement of fecal water content in mice with constipation after intervention with different substances, where *P<0.05, P<0.01 and *P<0.001 (vs the model group).

The results were shown in FIG. 27 that the *Lactobacillus buchneri* CCFM1053 can relieve constipation, increase the fecal water content and enable the fecal water content to be slightly higher than that of the control group.

Figure 28:
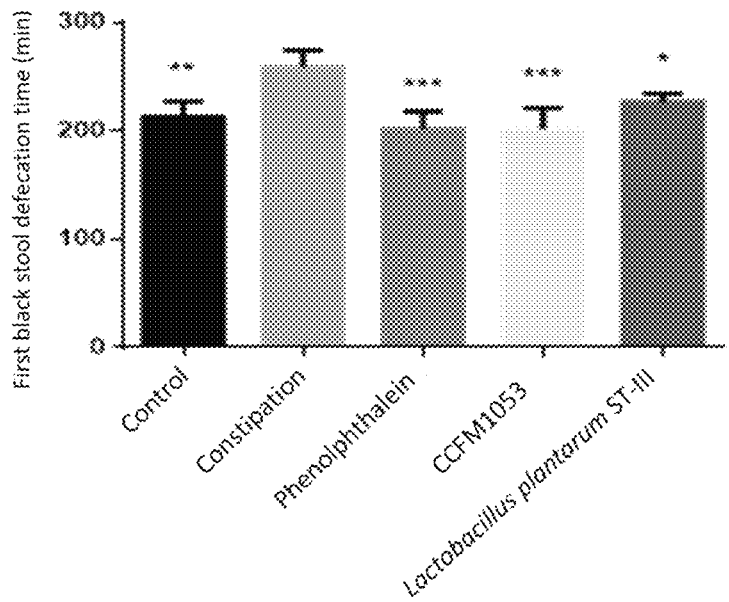
FIG. 28 shows decrease of first black stool defecation time in the mice with constipation after intervention with different substances, where *P<0.05, P<0.01 and *P<0.001 (vs the model group).

On the morning of the 17$^{th}$ day, the mice in the blank control group were gavaged with normal saline, the mice in the other groups were gavaged with loperamide, after the gavage for 1 h, all the mice were gavaged with 0.25 mL of an activated carbon arabic gum aqueous solution, each mouse was separately placed in a clean stainless steel cage covered with absorbent paper, time (min) from start of the gavage with the activated carbon to defecation of first black stool was recorded as first black stool defecation time to evaluate an effect of the *Lactobacillus buchneri* CCFM1053 on constipation of the mice, and during the period, the mice ate and drank freely. The results in FIG. 28 showed that the *Lactobacillus buchneri* CCFM1053 can shorten the first black stool defecation time and had an effect better than that of *Lactobacillus plantarum* ST-III.

Example 27 The *Lactobacillus buchneri* CCFM1053 can Promote Proliferation and MafA mRNA Expression of High Glucose-Induced INS-1 Cells In an experiment, 5 groups were divided: a normal group (a normal culture solution containing 11.1 mmol/L of glucose), a high glucose group (a high glucose culture solution containing 22.2 mmol/L of glucose), a rosiglitazone group (a high glucose culture solution+80 µmol/L of rosiglitazone), a CCFM1053 group (a high glucose culture solution+1×10$^9$ CFU/mL of a CCFM1053 bacterial solution) and an LGG group (a high glucose culture solution+1×10$^9$ CFU/mL of a LGG bacterial solution).

INS-1 cells (code: BH-AC0530) were cultured in a RPMI-1640 culture solution (containing 11.1 mmol/L of glucose, 10% of FBS, 50 µmol/L of 2-mercaptoethanol, 1 mmol/L of pyruvic acid and 10 mmol/L of HEPES) and placed in a 5% $CO_2$ incubator at 37° C.

Determination of cell proliferation by a CCK-8 assay: the cells in a good state were digested and centrifuged, the treated cells were inoculated on a 96-well plate with about 5×10$^3$ cells in each well, no cells were inoculated into peripheral wells of the plate to prevent an edge effect, and a PBS solution was added at the same time. After the cells adhered to walls, a RPMI-1640 medium containing 0.5% fetal bovine serum was added to each well, and a synchronized treatment was conducted for 24 h. At the end of the synchronization, corresponding medium was added into each well according to the grouping, culture was conducted for 48 h, three duplicate wells were arranged in each group and a zero-adjustment well was arranged. After drug intervention, an old medium was aspirated, the cells were washed twice with PBS, 180 µL of a serum-free medium and 20 µL of a CCK-8 solution were added, and the cells were incubated for 3-4 h. After the incubation, the absorbance of each well was measured at 450 nm by using a microplate reader.

Determination of MafA mRNA expression: RNA was extracted by a Trizol method, an original culture solution in a 6-well plate was discarded, the cells were washed twice with pre-cooled PBS, the cells were lysed by adding 1.0 mL of Trizol in each well, a lysate containing the cells was transferred to an enzyme-free EP tube, the lysate was pipetted until there was no obvious precipitate and standing was conducted for 5 min. 0.2 mL of chloroform was added to each EP tube, vigorous shaking was conducted for 15 s, and an obtained solution was placed at a room temperature for 2-3 min. The obtained solution was centrifuged at 12,000 rpm for 15 min at 4° C., about 0.4 mL of a supernatant was aspirated and transferred to another enzyme-free EP tube, 0.5 mL of isopropanol was added, an obtained mixture was inverted and mixed uniformly, and standing was conducted at a room temperature for 10 min. The standing solution was centrifuged at 12,000 rpm for 10 min at 4° C., a supernatant was discarded carefully, 1.0 mL of 75% ethanol was added and an obtained mixture was inverted and mixed uniformly. The obtained mixture was centrifuged at 12,000 rpm for 5 min at 4° C., a supernatant was discarded, and drying was conducted at a room temperature for 2-5 min. 20 µL of DEPC-treated water was added for dissolving and an obtained product was stored at 80° C. for standby use. The concentration and mass of RNA were determined and a reverse transcription was conducted according to the instructions of a reverse transcription kit. A cDNA obtained by the reverse transcription was detected by qRT-PCR, where MafA specific primers were as follows: F: 5'-atcactctgcc-caccatcac-3' (SEQ ID NO. 3) and R: 5'-atgacctcctccttgctgaa-3' (SEQ ID NO. 4). PCR system: F (10 µM), 0.50 µL; R (10 µM), 0.50 µL; c. DNA template, 1.00 µL; dd $H_2O$, 3.00 µL; and mix, 5.00 µL. PCR program was as follows: 95° C., 2 min; (95° C., 30 sec; 60° C., 30 sec; 72° C., 20 sec)*35; and 72° C., 5 min; and after the target gene was detected by real-time PCR, the relative gene expression was analyzed by a $2^{-\Delta\Delta CT}$ method. An expression level of a target gene in the INS-1 cells of each group of rats was analyzed by using a CFX Manager software, the expression level of the normal group was taken as 1, and compared with the normal group, the gene expression levels of other groups were calculated.

Figure 29:
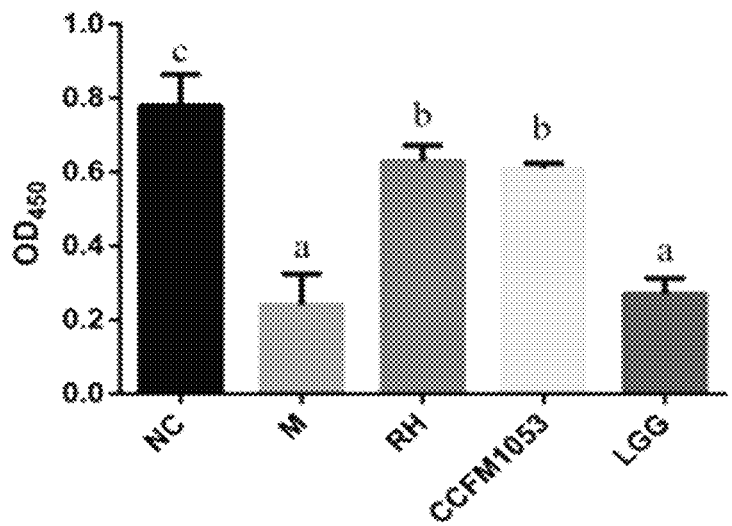
FIG. 29 shows effects of different substances on proliferation of INS-1 cells under high glucose.

The results of the CCK-8 assay were shown in FIG. 29. Compared with the normal group, the cell growth in the high glucose group was significantly decreased (P<0.05); the cell proliferation in the rosiglitazone control group was significantly increased compared with that in the high glucose group (P<0.05); and the cell proliferation in the CCFM1053 group was also significantly increased compared with that in the high glucose group (P<0.05).

Figure 30:
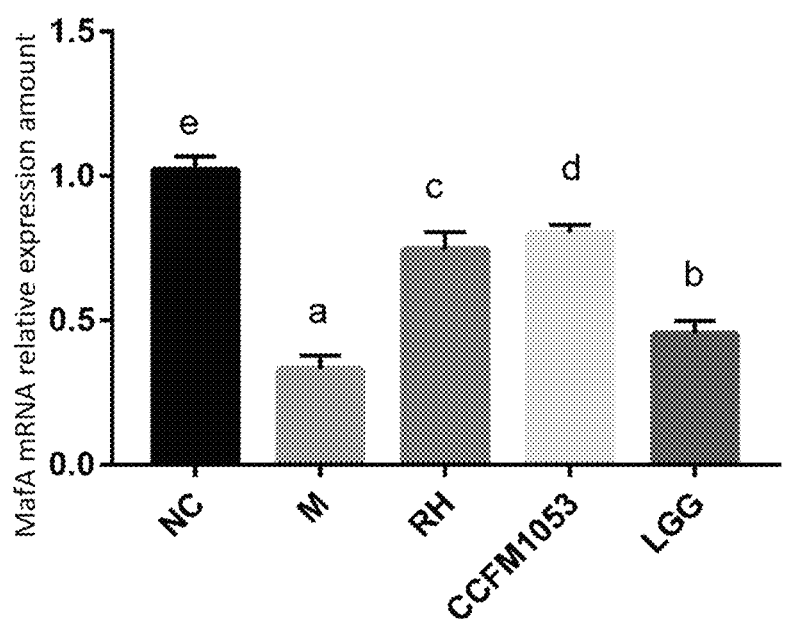
FIG. 30 shows effects of different substances on MafA gene expression of INS-1 cells under high glucose.

The expression of MafA mRNA was shown in FIG. 30. The expression of the MafA mRNA in the high glucose group was significantly lower than that in the normal group (P<0.05), while the expression of the MafA mRNA in the rosiglitazone positive control group and CCFM1053 group was significantly increased compared with that in the high glucose group (both P<0.05).

Example 28 Preparation of Fermented Food by Using *Lactobacillus buchneri* CCFM1053

(1) Preparation of fruit and vegetable drink

Fresh vegetables were selected, thoroughly cleaned, and juiced, and then high-temperature instant sterilization was performed. After high-temperature heat sterilization at 140° C. for 2 s, the temperature was immediately lowered to 37° C. Then the *Lactobacillus buchneri* CCFM1053 prepared in the disclosure was inoculated to make the concentration reach above 10$^6$ CFU/ml. The juice product was stored under refrigeration at 4° C., and thus, the fruit and vegetable beverage containing live bacteria of the *Lactobacillus buchneri* CCFM1053 of the disclosure was obtained. The fruit and vegetable product included cucumber, carrot, beet, celery and cabbage products.

(2) Preparation of fermented dairy product

The *Lactobacillus buchneri* CCFM1053 was inoculated into raw materials of a dairy product or a bean product to prepare a fermented dairy product or a fermented bean product; and the dairy product included milk, sour cream and cheese.

(3) The *Lactobacillus buchneri* CCFM1053 was inoculated into solid, semi-solid or liquid raw materials for fermentation to prepare a solid fermented food, a liquid fermented food and a semi-solid fermented food.

Similar to a use effect of the *Lactobacillus buchneri* CCFM1053, the fermented food prepared from the *Lactobacillus buchneri* CCFM1053 can significantly relieve spleen atrophy of the mice exposed to PFOA and significantly increase serum TNF-α content in the mice exposed to PFOA; and the *Lactobacillus buchneri* CCFM1053 significantly increases the content of serum ALT, AST and γ-GT of the mice exposed to PFOA, decreases the MDA content in the liver of the mice exposed to PFOA to a normal level, and reduces GSH activity, The *Lactobacillus buchneri* CCFM1053 obviously relieves intestinal flora disorder, reduces abundance of *Allobaculum* in the intestinal tract, increases abundance of *Bacteroides* and Eubacteriaceae, and reduces occurrence of liver disease. The *Lactobacillus buchneri* CCFM1053 can significantly improve fecal water content and decrease first black stool defecation time in the mice with constipation, and relieve constipation of the mice. The *Lactobacillus buchneri* CCFM1053 can also improve proliferation and MafA gene expression of INS-1 cells under high glucose and relieve PFOA-related diabetes.

Example 29 Preparation of Medicine Containing *Lactobacillus fermentum* CCFM1051

The *Lactobacillus fermentum* CCFM1051 was purified and activated, inoculated in an MRS liquid medium at an inoculation quantity of 1% (v/v), and cultured at 37° C. for 18 h. The bacteria were collected by centrifugation at 8,000 r/min for 5 min.

The *Lactobacillus fermentum* CCFM1051 was mixed with a pharmaceutically acceptable carrier to prepare a medicine.

The pharmaceutically acceptable carrier includes but is not limited to an excipient and the excipient includes but is not limited to lactose, dextrose, sucrose, sorbitol, mannitol, starch, arabic gum, calcium phosphate, alginate, tragacanth gum, gelatin, calcium silicate, microcrystalline cellulose, polyvinylpyrrolidone, cellulose, water, syrup and methylcellulose.

The pharmaceutically acceptable carrier includes but is not limited to prebiotics; and the prebiotics are selected from one or more of fructooligosaccharides, galactooligosaccharides and lactitol.

Example 30 Preparation of Medicine Containing *Lactobacillus casei* CCFM1052

The *Lactobacillus casei* CCFM1052 was purified and activated, inoculated in an MRS liquid medium at an inoculation quantity of 1% (v/v), and cultured at 37° C. for 18 h. The bacteria were collected by centrifugation at 8,000 r/min for 5 min.

The *Lactobacillus casei* CCFM1052 was mixed with a pharmaceutically acceptable carrier to prepare a medicine.

The pharmaceutically acceptable carrier includes but is not limited to an excipient and the excipient includes but is not limited to lactose, dextrose, sucrose, sorbitol, mannitol, starch, arabic gum, calcium phosphate, alginate, tragacanth gum, gelatin, calcium silicate, microcrystalline cellulose, polyvinylpyrrolidone, cellulose, water, syrup and methylcellulose.

The pharmaceutically acceptable carrier includes but is not limited to prebiotics; and the prebiotics are selected from one or more of fructooligosaccharides, galactooligosaccharides and lactitol.

Example 31 Preparation of Medicine Containing *Lactobacillus buchneri* CCFM1053

The *Lactobacillus buchneri* CCFM1053 was purified and activated, inoculated in an MRS liquid medium at an inoculation quantity of 1% (v/v), and cultured at 37° C. for 18 h. The bacteria were collected by centrifugation at 8,000 r/min for 5 min.

The *Lactobacillus buchneri* CCFM1053 was mixed with a pharmaceutically acceptable carrier to prepare a medicine.

The pharmaceutically acceptable carrier includes but is not limited to an excipient and the excipient includes but is not limited to lactose, dextrose, sucrose, sorbitol, mannitol, starch, arabic gum, calcium phosphate, alginate, tragacanth gum, gelatin, calcium silicate, microcrystalline cellulose, polyvinylpyrrolidone, cellulose, water, syrup and methylcellulose.

The pharmaceutically acceptable carrier includes but is not limited to prebiotics; and the prebiotics are selected from one or more of fructooligosaccharides, galactooligosaccharides and lactitol.

Example 32 Preparation of Medicine Containing Probiotics

The *Lactobacillus fermentum* CCFM1051, the *Lactobacillus casei* CCFM1052 and the *Lactobacillus buchneri* CCFM1053 were prepared into bacterial cells according to the following methods, respectively. Single colonies were activated in a liquid medium, inoculated in an MRS liquid medium at an inoculation quantity of 1% (v/v), and cultured at 37° C. for 18 h. The bacteria were collected by centrifugation at 8,000 r/min for 5 min.

One or more lactobacilli of the *Lactobacillus fermentum* CCFM1051, the *Lactobacillus casei* CCFM1052 and the *Lactobacillus buchneri* CCFM1053 were combined with other pharmaceutically or edibly acceptable probiotics to prepare a medicine.

The medicine further includes a pharmaceutically acceptable carrier and the pharmaceutically acceptable carrier includes but is not limited to an excipient and a diluent.

The excipient includes but is not limited to lactose, dextrose, sucrose, sorbitol, mannitol, starch, arabic gum, calcium phosphate, alginate, tragacanth gum, gelatin, calcium silicate, microcrystalline cellulose, polyvinylpyrrolidone, cellulose, water, syrup and methylcellulose; and The diluent includes but is not limited to normal saline or syrup.

Example 33 Preparation of Starter Containing Probiotics

The *Lactobacillus fermentum* CCFM1051, the *Lactobacillus casei* CCFM1052 and the *Lactobacillus buchneri* CCFM1053 were prepared into bacterial cells according to the following methods, respectively. Single colonies were activated in a liquid medium, inoculated in an MRS liquid medium at an inoculation quantity of 1% (v/v), and cultured at 37° C. for 18 h to prepare a fermentation agent.

Or the cell culture solution was centrifuged, *lactobacillus* cells were collected, and a cytoprotective agent was added to enable the probiotics to have a concentration of $\geq 1 \times 10^8$ CFU/mL.

Optionally, the cell suspension containing the cytoprotective agent was vacuum freeze-dried to obtain a powdered fermentation agent to enable the probiotics to have a concentration of $\geq 1 \times 10^8$ CFU/mL.

The cytoprotective agent includes but is not limited to a mixture of one or more of glycerol, DMSO, ethylene glycol, propylene glycol, acetamide, methanol, polyvinylpyrrolidone (PVP), sucrose, polyethylene glycol, dextran, albumin and hydroxyethyl starch.

Although the disclosure has been disclosed as above in the preferred examples, it is not intended to limit the disclosure. Any person skilled in the art can make various changes and modifications without departing from the spirit and scope of the disclosure. Therefore, the protection scope of the disclosure should be as defined in the claims.

What is claimed is:

1. A composition, comprising:
a cytoprotective agent selected from one or more of ethylene glycol, propylene glycol, polyvinylpyrrolidone (PVP), polyethylene glycol, and hydroxyethyl starch, and
one or more of the following lactobacilli:
(a) *Lactobacillus fermentum* CCFM1051, deposited in Guangdong Microbial Culture Collection Center on Apr. 29, 2019, and having the preservation number of GDMCC No: 60649;
(b) *Lactobacillus casei* CCFM1052, deposited in Guangdong Microbial Culture Collection Center on Apr. 29, 2019, and having the preservation number of GDMCC No: 60650; and
(c) *Lactobacillus buchneri* CCFM1053, deposited in Guangdong Microbial Culture Collection Center on Apr. 29, 2019, and having the preservation number of GDMCC No: 60651,
wherein the composition is freeze-dried.

2. The composition according to claim 1, wherein the fermentation composition is fermented by *Lactobacillus fermentum* CCFM1051, *Lactobacillus casei* CCFM1052, or *Lactobacillus buchneri* CCFM1053.

3. The composition according to claim 1, wherein the composition comprises the lactobacilli in an amount greater than or equal to $1\times10^8$ CFU/mL or in an amount greater than or equal to $1\times10^8$ CFU/g.

4. The composition according to claim 1, wherein the composition further comprises one or more pharmaceutically acceptable carriers.

5. The composition according to claim 4, wherein the one or more pharmaceutically acceptable carriers is selected from one or more of: lactose, dextrose, sorbitol, mannitol, starch, arabic gum, calcium phosphate, alginate, tragacanth gum, gelatin, calcium silicate, microcrystalline cellulose, cellulose, water, methylcellulose, saline, and syrup.

* * * * *